United States Patent
Takeuchi et al.

(10) Patent No.: US 7,285,640 B2
(45) Date of Patent: Oct. 23, 2007

(54) ANTIBODY TO STEM CELL FACTOR

(75) Inventors: Toshihiko Takeuchi, Oakland, CA (US); Adrian Tomkinson, Kensington, CA (US); Steven Neben, Walnut Creek, CA (US)

(73) Assignee: Bayer Corporation, Berkeley, CA (US)

( * ) Notice: Subject to any disclaimer, the term of this patent is extended or adjusted under 35 U.S.C. 154(b) by 296 days.

(21) Appl. No.: 10/320,231

(22) Filed: Dec. 16, 2002

(65) Prior Publication Data

US 2003/0194405 A1 Oct. 16, 2003

Related U.S. Application Data

(60) Provisional application No. 60/342,174, filed on Dec. 17, 2001.

(51) Int. Cl.
*C07K 16/00* (2006.01)
(52) U.S. Cl. .................... 530/387.1; 530/387.3
(58) Field of Classification Search .................... None
See application file for complete search history.

(56) References Cited

U.S. PATENT DOCUMENTS

2005/0112698 A1* 5/2005 Neben et al. ................ 435/7.2

FOREIGN PATENT DOCUMENTS

WO  WO94/11026  5/1994

OTHER PUBLICATIONS

Paul, Fundamental Immunology, (textbook), 1999, Immunoglobulins: Structure and Function, , pp. 37, 43, 58, 59.*
Rudikoff et al., Proc Natl Acad Sci USA 1982 vol. 79 p. 1979.*
Campbell, et al. "Stem Cell Factor-Induced Airway Hyperreactivity in Allergic and Normal Mice", *Am J. Pathol.*, vol. 154, pp. 1259-1265, 1999.
Finotto, et al., "Local administration of antisense phosphorothioate oligonucleotides to the c-kit ligand, stem cell factor, suppresses airway inflammation and IL-4 production in a murine model of asthma", *J. Allergy Clin. Immunol.*, vol. 107, pp. 279-286, 2001.
Knappik, et al., "Fully Synthetic Human Combinatorial Antibody Libraries (HuCAL) Based on Modular Consensus Frameworks and CDRs Randomized with Trinucleotides", *J. Mol. Biol.*, vol. 296, pp. 57-86, 2000.
Lukacs, et al, "Stem Cell Factor (c-*kit* Ligand) Influences Eosinophil Recruitment and Histamine Levels in Allergic Airway Inflammation", *J. Immunol.*, vol. 156, pp. 3945-3950, 1996.

* cited by examiner

*Primary Examiner*—Michail Belyavskyi
(74) *Attorney, Agent, or Firm*—DLA Piper US LLP

(57) ABSTRACT

The present invention provides human antibodies specific for stem cell factor that contain at least one CDR derived from a combinatorial antibody library. The invention also provides pharmaceutical compositions comprising the antibodies and methods of treating asthma. The invention further provides methods of detecting stem cell factor using the antibodies.

7 Claims, 2 Drawing Sheets

Vector map of pMORPHx9_Fab1_FS

Fab display vector pMORPH18 Fab 1

ANTIBODY TO STEM CELL FACTOR

CROSS-REFERENCE TO RELATED APPLICATIONS

This application claims the benefit of U.S. Provisional Application 60/342,174 filed Dec. 17, 2001, which is hereby incorporated herein in its entirety by reference.

FIELD OF THE INVENTION

The present invention relates to antibodies and treatments for asthma and other disorders in which stem cell factor protein is expressed in certain cells. More specifically, the present invention relates to human antibodies that inhibit stem cell factor activity, polynucleotide sequences encoding the antibodies, and use of the antibodies in the treatment of asthma and other disorders in which stem cell factor is expressed in certain cells.

BACKGROUND OF THE INVENTION

Allergic asthma is characterized by variable reversible airway obstruction, and airway hyperresponsiveness associated with airway inflammation. The inflammation is itself characterized by the presence of activated mast cells and eosinophils, which through the generation of proinflammatory mediators and cytokines play a fundamental role in the pathogenesis of the disease. The eosinophil is thought to be a major effector cell in the development of airway hyperresponsiveness, through the release of cytotoxic granule proteins. However, the initial induction of IgE-mediated mast cell activation/degranulation constitutes the primary mechanism that drives the allergic airway response and changes in airway physiology. Activation of mast cells by cross linking of IgE leads to the release of histamine and generation of leukotrienes that appear to contribute to the early bronchoconstriction occurring within minutes of allergen exposure. Moreover, the production of cytokines (TNF, IL-4, IL-5), angiogenic and fibrotic factors, and the release of chemokines (RANTES, eotaxin, MCP-1, TARC) which favor the infiltration of the airway tissues with eosinophils and lymphocytes, drive/enhance the maintenance and progression of the disease. The relationship between mast cell activation and eosinophil recruitment has substantial consequences on the pathogenesis of asthma.

Stem Cell Factor (SCF; also known as Mast Cell Growth Factor, Steel Factor or c-kit ligand) is an important hematopoietic factor that drives the differentiation of mast cells in the bone marrow. SCF as a result of alternate splicing exists as a membrane bound and soluble form and is produced by bone marrow stromal cells. SCF is also produced by several cell types found in peripheral tissues including fibroblasts, endothelial cells, epithelial cells, mast cells and eosinophils, and is thought to be the primary cytokine regulating the survival, activation, and degranulation of mature mast cells in the lung microenvironment. In addition to IgE mediated activation of mast cells, SCF can directly induce mast cell activation and degranulation resulting in the release of inflammatory mediators, cytokines and chemokines as discussed above. Moreover, SCF strongly augments the IgE-mediated activation of mast cells. The prolonged activation of local airway mast cell populations by SCF after initial IgE-mediated activation may play a significant role in persistent activation leading to prolonged impairment of lung function. SCF also induces mast cell adhesion to extra cellular matrix proteins as well as their chemotaxis. SCF has also demonstrated a direct role on eosinophil adhesion by altering avidity of VLA-4 on the surface of eosinophils which has significant consequences for eosinophil migration to the lung.

In vivo administration of SCF to the airways has been shown to be a potent inducer of airway hyperreactivity and inflammation in mice (Lukacs et al., *J. Immunol.*, 156: 3945 (1996); Campbell et al., *Am. J. Pathol.*, 154:1259 (1999). Recently, published studies have demonstrated therapeutic benefit of inhibitors of SCF, either antibodies or antisense RNA, in treating antigen-induced asthma in rodent models (Campbell et al., *Am. J. Pathol.*, 154:1259 (1999).; Finotto et al., *J. Allergy Clin. Immunol.*, 107:279 (2001)).

It is an object of the invention to provide reagents and methods of inhibiting stem cell factor activity.

SUMMARY OF THE INVENTION

The invention provides human antibodies that bind to stem cell factor. These antibodies are useful for a variety of therapeutic and diagnostic purposes, including the treatment of asthma.

The invention provides a purified human antibody which binds to stem cell factor protein, the antibody comprising a light chain variable region comprising an amino acid sequence selected from the group consisting of SEQ ID NOS: 19-24 or a heavy chain variable region comprising an amino acid sequence selected from the group consisting of SEQ ID NOS: 13-18, the antibody being optionally bound to a cytotoxic molecule or detectable label. In other embodiments, the antibody comprises heavy and light chain variable regions comprising a pair of amino acid sequences selected from the group consisting of SEQ ID NOS: 13 and 19, SEQ ID NOS: 14 and 20, SEQ ID NOS: 15 and 24, SEQ ID NOS: 16 and 21, SEQ ID NOS: 17 and 22 and SEQ ID NOS: 18 and 23.

The heavy and light chain variable regions of the antibody can comprise framework residues from native human antibodies, but preferably the heavy and light chain variable region framework are comprised of consensus framework residues. More preferably, the heavy chain variable region comprises human VH3 consensus framework residues. The light chain variable region can comprise either human Vκ1 consensus framework residues or human Vλ1 consensus framework residues.

In a preferred embodiment of the invention the antibody comprises heavy and light chain variable regions comprising SEQ ID NOS: 14 and 20. The antibody can also comprise a light chain variable region comprising an amino acid sequence selected from the group consisting of SEQ ID NOS: 57, 59, 61, 63 and 65 and a light chain variable region comprising an amino acid sequence selected from the group consisting of SEQ ID NOS: 67, 69, 71, 73 and 75. More preferably the antibody comprises a heavy chain variable region comprising SEQ ID NO: 14, a light chain variable region comprising SEQ ID NO: 20, a light chain variable region comprising SEQ ID NO: 59, and a light chain variable region comprising SEQ ID NO: 69.

The invention also provides a preparation comprising the antibodies of the invention. The purified preparations can contain one or more different antibodies of the invention.

Another aspect of the invention provides a pharmaceutical composition comprising the antibody of the invention and a pharmaceutically acceptable carrier.

A further aspect of the invention provides an isolated polynucleotide or nucleotides encoding the antibodies. The antibodies of the invention typically contain light and heavy chains, and the sequences encoding the light and heavy chains can be contained in one polynucleotide or in two or more polynucleotides.

An additional aspect of the invention provides an expression vector comprising the purified polynucleotide or polynucleotides encoding the antibodies, and host cells comprising the expression vector. The invention further provides a method of producing a human antibody, comprising the steps of: culturing a host cell comprising an expression vector of the invention under conditions whereby the antibody is expressed; and purifying the antibody from the host cell or host cell culture medium.

Yet another aspect of the invention provides a method of treating a human disorder in which stem cell factor protein is expressed in certain cells, preferably asthma, comprising the steps of administering to a mammal, preferably a human, in need of such treatment an effective amount of a human stem cell factor antibody of the invention wherein the antibody is bound to a cytotoxic molecule, which cytotoxic molecule is capable of inducing apoptosis in the stem cell factor expressing cells.

A further aspect of the invention provides a method of treating a human disorder in which stem cell factor protein is expressed in certain cells, preferably asthma comprising the steps of administering to a mammal, preferably a human, in need of such treatment an effective amount of a human stem cell factor antibody of the invention.

These and other aspects of the invention are set out the appended claims and in the following detailed description.

DETAILED DESCRIPTION OF THE INVENTION

Figure 1:
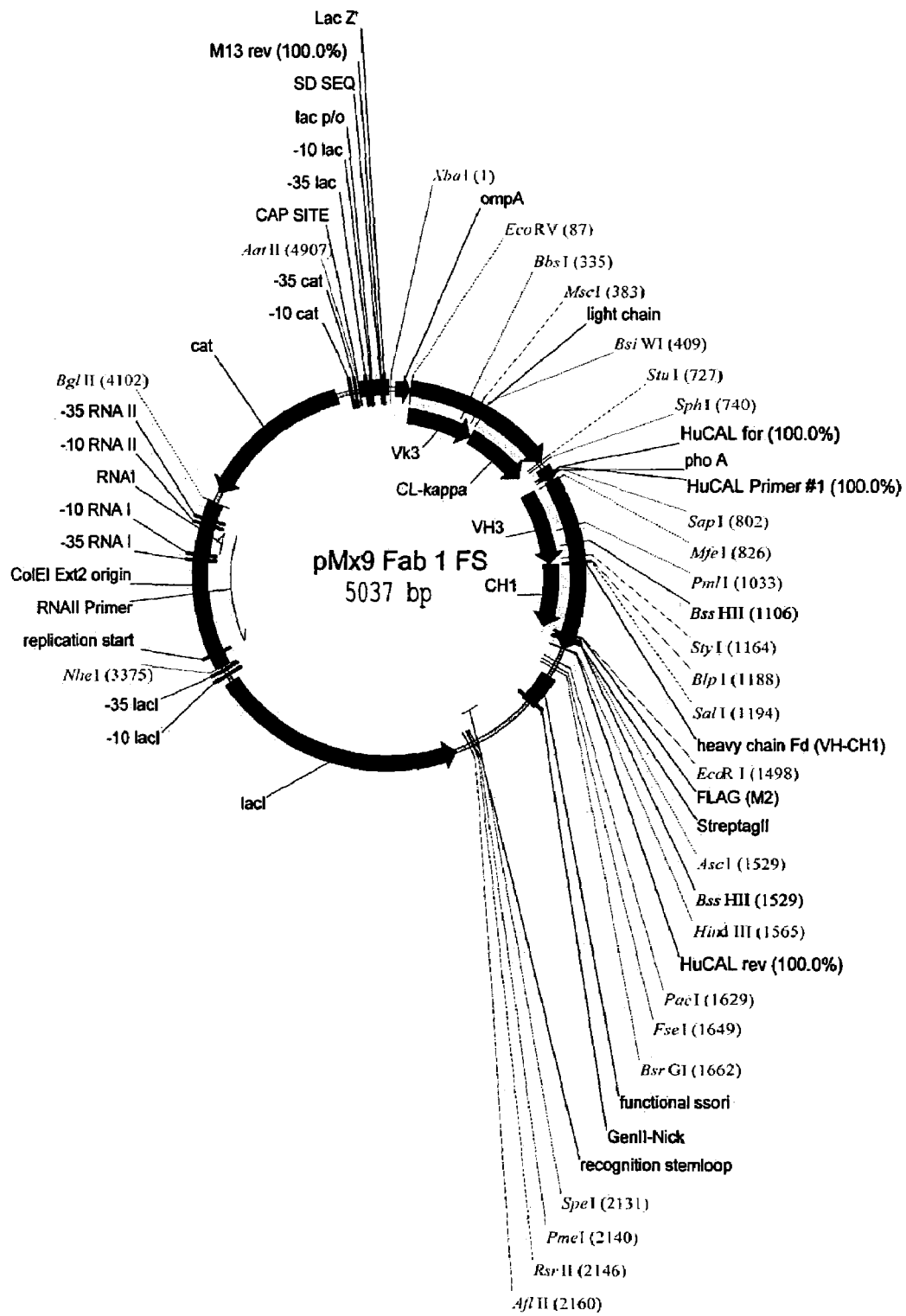
FIG. 1 Vector map of pMORPHx9_Fab1_FS.

It is an object of the invention to provide reagents and methods of inhibiting stem cell factor activity. This and other objects of the invention are provided by one or more of the embodiments set out below.

Naturally occurring antibodies (immunoglobulins) comprise two heavy chains linked together by disulfide bonds and two light chains, one light chain being linked to each of the heavy chains by disulfide bonds. Each heavy chain has at one end a variable domain ($V_H$) followed by a number of constant domains. Each light chain has a variable domain ($V_L$) at one end and a constant domain at its other end, the constant domain of the light chain is aligned with the first constant domain of the heavy chain, and the light chain variable domain is aligned with the variable domain of the heavy chain. Particular amino acid residues are believed to form an interface between the light and heavy chain variable domains, see e.g. Chothia et al., J. Mol. Biol. 186:651-663 (1985); Novotny and Haber, Proc. Natl. Acad. Sci. USA 82:4592-4596 (1985).

The constant domains are not involved directly in binding the antibody to an antigen, but are involved in various effector functions, such as participation of the antibody in antibody-dependent cellular cytotoxicity. The variable domains of each pair of light and heavy chains are involved directly in binding the antibody to the antigen. The domains of natural light and heavy chains have the same general structure, and each domain comprises four framework (FR) regions, whose sequences are somewhat conserved, connected by three hyper-variable or complementarity determining regions (CDRs) (see Kabat, E. A. et a., Sequences of Proteins of Immunological Interest, National Institutes of Health, Bethesda, Md., (1987)). The four framework regions largely adopt a beta-sheet conformation and the CDRs form loops connecting, and in some cases forming part of, the beta-sheet structure. The CDRs in each chain are held in close proximity by the framework regions and, with the CDRs from the other chain, contribute to the formation of the antigen binding site.

"Antibody" as used herein includes intact immunoglobulin molecules (e.g., IgG1, IgG2a, IgG2b, IgG3, IgM, IgD, IgE, IgA), as well as fragments thereof, such as Fab, F(ab')$_2$, scFv, and Fv, which are capable of specific binding to an epitope of a human Stem Cell Factor protein. "Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments. Antibodies that specifically bind to Stem Cell Factor provide a detection signal at least 5-, 10-, or 20-fold higher than a detection signal provided with other proteins when used in an immunochemical assay. Preferably, antibodies that specifically bind to human Stem Cell Factor do not detect other proteins in immunochemical assays and can immunoprecipitate the Stem Cell Factor from solution.

In general, the antibodies of the invention will comprise substantially all of at least one, and typically two, variable domains (such as Fab, Fab', F(ab').sub.2, Fabc, Fv) in which one or more of the CDR regions are synthetic amino acid sequences that bind with Stem Cell Factor, and all or substantially all of the framework regions are those of a human immunoglobulin consensus sequence. The framework regions can also be those of a native human immunoglobulin sequence. Other CDR regions in the antibody can be selected to have human immunoglobulin consensus sequences for such CDRs or the sequence of a native human antibody. The antibody optimally also will comprise at least a portion of an immunoglobulin constant region (Fc) of a human immunoglobulin. Ordinarily, the antibody will contain both the light chain as well as at least the variable domain of a heavy chain. The antibody also may include the CH1, hinge, CH2, CH3, and CH4 regions of the heavy chain.

The antibody will be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the antibody exhibit cytotoxic activity, and the class is typically IgG$_1$. Where such cytotoxic activity is not desirable, the constant domain may be of the IgG$_2$ class. The antibody may comprise sequences from more than one class or isotype, and selecting particular constant domains to optimize desired effector functions is within the ordinary skill in the art. The sequences of human immunoglobulin heavy and light chains are known in the art. The variable regions can also be selected from human immunoglobulin consensus sequences known in the art, such as the sequences disclosed in Knappik et al., J. Mol. Biol. 296, 57-86 (2000) and U.S. Pat. No. 6,300,064.

The dissociation constant ($K_d$) of human antibody binding to Stem Cell Factor can be assayed using any method known in the art, including technologies such as real-time Bimolecular Interaction Analysis (BIA) (Sjolander & Urbaniczky, Anal. Chem. 63, 2338-2345, 1991, and Szabo et al., Curr. Opin. Struct. Biol. 5, 699-705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In a BIAcore™ assay as described above in Sjolander & Urbaniczky (1991) and Szabo et al. (1995) human antibodies of the present invention specifically bind to human Stem Cell Factor with a $K_d$ in the range from about 1 nM ($1 \times 10^{-9}$ M) to about 70 nM ($70 \times 10^{-8}$ M). More preferred human antibodies of the present invention specifically bind to human Stem Cell Factor with a $K_d$ of approximately 4 nM to about 50 nM, with the most preferred antibodies of this invention binding human Stem Cell Factor protein with a $K_d$ of approximately 1 nM.

Additionally, human antibodies of this invention will preferably bind Stem Cell Factor and neutralize its biological activity with an $IC_{50}$ ranging from about 10 μg/ml to 30 μg/ml. More preferred human antibodies bind Stem Cell Factor and neutralize its biological activity with an $IC_{50}$ ranging from approximately 1 μg/ml to 3 μg/ml, with the most preferred antibodies of this invention neutralizing activity of human Stem Cell Factor protein with an $IC_{50}$ of approximately 0.1 μg/ml to 0.3 μg/ml. $IC_{50}$ is the dose that effectively neutralizes 50% of the biological response induced by human stem cell factor. ($IC_{50}$ can also refer to the inhibitory or effective concentration causing 50% of the maximum response induced by stem cell factor.)

This invention uses Morphosys phage-antibody technology to generate fully human antibodies against the Stem Cell Factor protein in accordance with the method of Knappik et al., *J. Mol. Biol.* 296, 57-86 (2000) and U.S. Pat. No. 6,300,064. Briefly, a fully synthetic human combinatorial antibody library (HuCAL) based on modular consensus frameworks and CDRs randomized with trinucleotides is screened to identify antibodies that bind to stem cell factor. The library is based upon human backbones, greatly reducing the probability of immunogenicity. A number of human antibodies having the Stem Cell Factor binding characteristics described above have been identified by screening the MorphoSys HuCAL Fab library. The randomized CDR cassettes assembled for the HuCAL library were designed to achieve a length distribution ranging from 5 to 28 amino acid residues, covering the stretch from position 95 to 102. A number of human antibodies having the Stem Cell Factor binding characteristics described above have been identified by screening the MorphoSys HuCAL Fab library. Generally, the CDR3 region is first randomized, and antibodies identified as specific for the test protein are then optimized by randomizing the CDR1 and/or CDR2 regions of such antibodies to identify additional antibodies with more desirable binding profiles.

Human antibodies with the Stem Cell Factor binding activity described above can be identified from the MorphoSys HuCAL library as follows. Human Stem Cell Factor is coated on a microtiter plate and incubated with the MorphoSys HuCAL-Fab phage library (see Example 1). Those phage-linked Fabs not binding to Stem Cell Factor can be washed away from the plate, leaving only phage that tightly bind to Stem Cell Factor. The bound phage can be eluted by a change in pH and amplified by infection of *E. coli* hosts. This panning process can be repeated once or twice to enrich for a population of phage-linked antibodies that tightly bind to Stem Cell Factor. The Fabs from the enriched pool are then expressed, purified, and screened in an ELISA assay. The identified hits are then tested for binding using a BIAcore™ assay, and these hits can be further screened in the cell adhesion assay as described above.

The initial panning of the HuCAL-Fab library also can be performed with Stem Cell Factor as the antigen in round one, followed in round 2 by Stem Cell Factor peptides fused to carrier proteins, such as BSA or transferrin, and in round 3 by Stem Cell Factor antigen again. Human Stem Cell Factor peptides that can be used for panning include the amino acid shown in SEQ I.D. NO: 25.

Details of the screening process are described in the Examples 2, 3 and 4. Other selection methods for highly active specific antibodies or antibody fragments can be envisioned by those skilled in the art and used to identify human Stem Cell Factor antibodies.

In some embodiments of the invention, the CDR3 of the heavy chain, which heavy chain preferably comprises a VH3 consensus heavy chain, has an amino acid sequence shown in SEQ ID NOS: 13-18. In other embodiments of the invention, the CDR3 region of the light chain has an amino acid sequence shown in SEQ ID NOS: 19-23. In such embodiments the light chain variable region preferably comprises a VLκ1 consensus variable region. In additional embodiments of the invention, the CDR3 region of the light chain has the amino acid sequence shown in SEQ ID NO: 24, and the light chain is preferably comprised of a VLλ1 consensus variable region. Human antibodies that have Stem Cell Factor binding activity are as shown in Table 3. The consensus variable regions for antibodies with Stem Cell Factor binding activity are shown in Tables 1 and 2.

In other embodiments of the invention, the antibody comprises heavy and light chain variable regions comprising a pair of amino acid sequences selected from the group consisting of SEQ ID NOS: 13 and 19, SEQ ID NOS: 14 and 20, SEQ ID NOS: 15 and 24, SEQ ID NOS: 16 and 21, SEQ ID NOS: 17 and 22 and SEQ ID NOS: 18 and 23. In each pair of sequences, the first sequence is preferably in the heavy chain CDR3 region and the second sequence is preferably in the light chain CDR3 region.

In preferred embodiments, the antibody comprises heavy and light chain variable regions comprising the pair of amino acid sequences SEQ ID NOS: 14 and 20, wherein SEQ ID NO: 14 is in the heavy chain CDR3 region and SEQ ID NO: 20 is in the light chain CDR3 region. Such preferred antibodies can also contain a light chain variable region, corresponding to the CDR1 region, comprising an amino acid sequence selected from the group consisting of SEQ ID NOS: 57, 59, 61, 63 or 65, and a light chain variable region, corresponding to the CDR2 region, comprising an amino acid sequence selected from the group consisting of SEQ ID NOS: 67, 69, 71, 73 and 75.

More preferably, the antibody comprises a heavy chain variable region comprising SEQ ID NO: 14, a light chain variable region comprising SEQ ID NO: 20, a light chain variable region comprising SEQ ID NO: 59, and a light chain variable region comprising SEQ ID NO: 69. A preferred antibody of the invention comprises light chain variable and constant regions as shown in SEQ ID NO: 77, and heavy chain variable and constant regions as shown in SEQ ID NO: 79.

Human antibodies with the characteristics described above also can be purified from any cell that expresses the antibodies, including host cells that have been transfected with antibody-encoding expression constructs. The host cells are cultured under conditions whereby the human antibodies are expressed. The antibodies can then be purified from the host cells or cell culture medium. Suitable methods include, but are not limited to, size exclusion chromatography, ammonium sulfate fractionation, ion exchange chromatography, affinity chromatography, and preparative gel electrophoresis.

A purified antibody is one which has been separated from other compounds that normally associate with the antibody in the cell, such as certain proteins, carbohydrates, or lipids or separated from reagents used for chemical synthesis of the antibody, using methods well known in the art. Such methods include, but are not limited to, size exclusion chromatography, ammonium sulfate fractionation, ion exchange chromatography, affinity chromatography, and preparative gel electrophoresis. In preferred embodiments, the antibody will be purified (1) to at least 70% by weight of antibody as determined by the Lowry method, more preferably 80%, 90%, 95% or 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain.

A preparation of the antibodies comprises at least one type of antibody of the invention in a purified form, wherein the antibodies preferably comprise at least 70% by weight of the total protein in the preparation, more preferably, 80%, 90%, 95% or 99% by weight of the total protein in the preparation. Purity of the preparations can be assessed by any means known in the art, such as SDS-polyacrylamide gel electrophoresis. A preparation of purified human antibodies of the invention can contain more than one type of human antibody with the Stem Cell Factor binding and neutralizing characteristics described above.

Alternatively, human antibodies can be produced using chemical methods to synthesize its amino acid sequence, such as by direct peptide synthesis using solid-phase techniques (Merrifield, *J. Am. Chem. Soc.* 85, 2149-2154, 1963; Roberge et al., *Science* 269, 202-204, 1995). Protein synthesis can be performed using manual techniques or by automation. Automated synthesis can be achieved, for example, using Applied Biosystems 431A Peptide Synthesizer (Perkin Elmer). Optionally, fragments of human antibodies can be separately synthesized and combined using chemical methods to produce a full-length molecule.

The newly synthesized molecules can be substantially purified by preparative high performance liquid chromatography (e.g., Creighton, PROTEINS: STRUCTURES AND MOLECULAR PRINCIPLES, W H Freeman and Co., New York, N.Y., 1983) or other methods known in the art. The composition of a synthetic polypeptide can be confirmed by amino acid analysis or sequencing (e.g., using Edman degradation).

The invention also provides polynucleotides encoding human stem cell factor antibodies. These polynucleotides can be used, for example, to produce quantities of the antibodies for therapeutic or diagnostic use. The antibodies of the invention typically contain light and heavy chains, and the sequences encoding the light and heavy chains can be contained in one polynucleotide or in two or more polynucleotides. The polynucleotides can be DNA or RNA.

Polynucleotides that can be used to encode the CDR3 regions of SEQ ID NOS: 13-24 are shown in SEQ ID NOS: 1-13. Polynucleotides that encode consensus heavy chains and light chains of human antibodies that have been isolated from the Morphosys HuCAL library are shown in Table 1 (SEQ ID NOS: 26-39). Polynucleotides that can be used to encode the CDR1 and CDR2 regions are shown in Table 5. Polynucleotides encoding human immunoglobulin light and heavy chains are known in the art. Any combination of native human immunoglobulin light and heavy chains or consensus sequences can be used in the production of the antibodies of the invention.

Polynucleotides of the invention present in a host cell can be isolated from other cellular components such as membrane components, proteins, and lipids. The polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated polynucleotides encoding antibodies of the invention. For example, restriction enzymes and probes can be used to isolate polynucleotides which encode the antibodies. Isolated polynucleotides are in preparations that are free or at least 70, 80, or 90% free of other molecules.

Human antibody-encoding cDNA molecules of the invention can be made with standard molecular biology techniques, using mRNA as a template. Thereafter, cDNA molecules can be replicated using molecular biology techniques known in the art and disclosed in manuals such as Sambrook et al., *Molecular Cloning: A Laboratory Manual*, Cold Spring Harbor Laboratory Press, Cold Spring Harbor, N.Y., USA (1989). An amplification technique, such as PCR, can be used to obtain additional copies of the polynucleotides.

Alternatively, synthetic chemistry techniques can be used to synthesize polynucleotides encoding antibodies of the invention. The degeneracy of the genetic code allows alternate nucleotide sequences to those depicted in SEQ ID NOS: 1-6, 7-11, or 12 to be synthesized that will encode an antibody having, for example, one of the VH3-CDR3, VLκ-CDR3, VLλ-CDR3 amino acid sequences shown in SEQ ID NOS: 13-18, 19-23, or 24, respectively.

To express a polynucleotide encoding a human antibody of the invention, the polynucleotide can be inserted into an expression vector that contains the necessary elements for the transcription and translation of the inserted coding sequence. Expression vectors of the invention thus comprise a polynucleotide or polynucleotides encoding the antibody and at least one element necessary for the transcription and translation of the coding sequence, such as a promoter operably linked to the coding sequence. Methods that are well known to those skilled in the art can be used to construct expression vectors containing sequences encoding human antibodies and appropriate transcriptional and translational control elements. These methods include in vitro recombinant DNA techniques, synthetic techniques, and in vivo genetic recombination. Such techniques are described, for example, in Sambrook et al. (1989) supra and in Ausubel et al., CURRENT PROTOCOLS IN MOLECULAR BIOLOGY, John Wiley & Sons, New York, N.Y., 1995. See also Examples 1-3, below.

A variety of expression vector/host systems can be utilized to contain and express sequences-encoding a human antibody of the invention. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems, such as CHO-K1 cells or HKB11 cells described in U.S. Pat. No. 6,136,599 and the vectors described therein. HKB11 cells and vectors described in U.S. Pat. No. 6,136,599 are a preferred expression vector/host cell system.

The control elements or regulatory sequences are those non-translated regions of the vector, including enhancers, promoters, and 5' and 3' untranslated regions, which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a human antibody, vectors based on SV40 or EBV can be used with an appropriate selectable marker.

To assess the efficacy of a particular antibody in allergic asthma therapy, the antibody can be tested in vitro in TF-1 proliferation and eosoniphil survival assays as detailed in Examples 7 & 8, respectively. In addition, the ability of Stem Cell Factor antibodies to inhibit Stem Cell Factor activity can be measured in vivo with a cynomologous monkey model.

Any of the human Stem Cell Factor antibodies described above can be provided in a pharmaceutical composition comprising a pharmaceutically acceptable carrier. The pharmaceutically acceptable carrier preferably is non-pyrogenic. The compositions can be administered alone or in combination with at least one other agent, such as stabilizing compound, which can be administered in any sterile, biocompatible pharmaceutical carrier, including, but not limited to, saline, buffered saline, dextrose, and water. A variety of aqueous carriers may be employed, e.g., 0.4% saline, 0.3% glycine, and the like. These solutions are sterile and generally free of particulate matter. These solutions may be sterilized by conventional, well-known sterilization techniques (e.g., filtration). The compositions may contain pharmaceutically acceptable auxiliary substances as required to approximate physiological conditions such as pH adjusting and buffering agents, etc. The concentration of the antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected. See U.S. Pat. No. 5,851,525. If desired, more than one type of human antibody, for example with different $K_d$ for Stem Cell Factor binding, can be included in a pharmaceutical composition.

The compositions can be administered to a patient alone, or in combination with other agents, drugs or hormones. In addition to the active ingredients, these pharmaceutical compositions can contain suitable pharmaceutically acceptable carriers comprising excipients, and auxiliaries that facilitate processing of the active compounds into preparations which can be used pharmaceutically. Pharmaceutical compositions of the invention can be administered by any number of routes including, but not limited to, oral, intravenous, intratracheal, inhalation, intramuscular, intra-arterial, intramedullary, intrathecal, intraventricular, transdermal, subcutaneous, intraperitoneal, intranasal, parenteral, topical, sublingual, or rectal means.

After pharmaceutical compositions have been prepared, they can be placed in an appropriate container and labeled for treatment of an indicated condition. Such labeling would include amount, frequency, and method of administration.

The invention also provides methods of ameliorating symptoms of a disorder in which Stem Cell Factor is elevated. These disorders include, without limitation, asthma and other immunological or allergic disorders. In one embodiment of the invention, a therapeutically effective dose of a human antibody of the invention is administered to a patient having a disorder in which Stem Cell Factor activity is elevated, such as those disorders above.

The determination of a therapeutically effective dose is well within the capability of those skilled in the art. A therapeutically effective dose refers to the amount of human antibody that is used to effectively treat asthma or other disorder in which stem cell factor is elevated compared with the efficacy that is evident in the absence of the therapeutically effective dose.

The therapeutically effective dose can be estimated initially in animal models, usually rats, mice, rabbits, dogs, pigs or non-human primates. The animal model also can be used to determine the appropriate concentration range and route of administration. Such information can then be used to determine useful doses and routes for administration in humans. An experimental mouse model of allergic asthma is described in Example 9.

Therapeutic efficacy and toxicity, e.g., $ED_{50}$ (the dose therapeutically effective in 50% of the population) and $LD_{50}$ (the dose lethal to 50% of the population) of a human antibody, can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the patient who requires treatment. Dosage and administration are adjusted to provide sufficient levels of the human antibody or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Polynucleotides encoding human antibodies of the invention can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding the antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

The mode of administration of human antibody-containing pharmaceutical compositions of the invention can be any suitable route which delivers the antibody to the host. Pharmaceutical compositions of the invention are particularly useful for parenteral administration, i.e., subcutaneous, intramuscular, intravenous, or intranasal administration.

The antibodies of the invention can also be bound to a cytotoxic molecule such as a chemotherapeutic agent, a toxin (such as an enzymatically active toxin of bacterial, fungal, plant or animal origin, or fragments thereof), or a radioactive isotope (i.e., a radioconjugate). Preferably, the cytotoxic molecule is capable of inducing apoptosis in stem cell factor expressing cells upon administration of the antibody with bound cytotoxic molecule. Antibodies of the invention bound to a cytotoxic molecule can be used in the same manner as antibodies without a bound cytotoxic molecule, with adjustments to the dose, route of administration and dosing regimen depending on the type of cytotoxic molecule employed.

Suitable chemotherapeutic agents include adriamycin, doxorubicin, 5-fluorouracil, cytosine arabinoside ("Ara-C"), cyclophosphamide, thiotepa, taxotere (docetaxel), busulfan, cytoxin, taxol, methotrexate, cisplatin, melphalan, vinblastine, bleomycin, etoposide, ifosfamide, mitomycin C, mitoxantrone, vincreistine, vinorelbine, carboplatin, teniposide, daunomycin, carminomycin, aminopterin, dactinomycin, mitomycins, esperamicins, taxane and maytansin derivatives. Enzymatically active toxins and fragments thereof which can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugated antibodies including $^{212}$Bi, $^{131}$I, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

The invention also provides diagnostic methods, with which human Stem Cell Factor can be detected in a test preparation, including without limitation a sample of serum, broncheoalveolar lavage fluid, lung, a cell culture system, or a cell-free system (e.g., a tissue homogenate). Such diagnostic methods can be used, for example, to diagnose disorders in which Stem Cell Factor is altered. When used for diagnosis, detection of an amount of the antibody-Stem Cell Factor complex in a test sample from a patient which varied with that of an amount of the complex in a normal sample identifies the patient as likely to have the disorder. The test preparation is contacted with a human antibody of the invention, and the test preparation is then assayed for the presence of an antibody-Stem Cell Factor complex. Suitable assay formats include those described herein for detecting Stem Cell Factor or antibodies of the invention.

The invention also provides methods for detecting Stem Cell Factor or antibodies to Stem Cell Factor. The methods comprise the steps of adding an antibody of the invention to a test sample suspected of containing Stem Cell Factor and detecting antibody bound to Stem Cell Factor, whereby the presence of bound antibody indicates the presence of Stem Cell Factor in the test sample. Alternatively, the invention provides methods for detecting antibodies of the invention comprising adding Stem Cell Factor to a test sample suspected of containing antibodies of the invention and detecting Stem Cell Factor bound to antibodies of the invention, whereby the presence of bound Stem Cell Factor indicates the presence of antibodies of the invention in the test sample.

Numerous formats for immunoassays are known in the art, including, for example, competitive binding assays, direct and indirect sandwich assays, and immuno-precipitation assays.

If desired, the human antibody can comprise a detectable label, such as a fluorescent, radioisotopic, chemiluminescent, or enzymatic label, such as horseradish peroxidase, alkaline phosphatase, or luciferase.

Optionally, the antibody can be bound to a solid support, which can accommodate automation of the assay. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the antibody to the solid support, including use of covalent and non-covalent linkages, passive absorption, or pairs of binding moieties attached to the antibody and the solid support. Binding of Stem Cell Factor and the antibody can be accomplished in any vessel suitable for containing the reactants. Examples of such vessels include microtiter plates, test tubes, and microcentrifuge tubes.

Suitable radioisotopic labels include radioisotopes, such as $^{35}$S, $^{14}$C, $^{125}$I, $^{3}$H, and $^{131}$I. The antibody can be labeled with the radioisotope using the techniques described in Current Protocols in Immunology, Volumes 1 and 2, Coligen et al., Ed. Wiley-Interscience, New York, N.Y., Pubs. (1991) for example and radioactivity can be measured using scintillation counting.

Suitable fluorescent labels include rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

Suitable enzymatic labels include luciferases (e.g., firefly luciferase and bacterial luciferase, luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocydic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, N.Y., 73: 147-166 (1981). Examples of enzyme-substrate combinations include, for example: Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); alkaline phosphatase (AP) with para-Nitrophenyl phosphate as chromogenic substrate; and beta.-D-galactosidase (.beta.-D-Gal) with a chromogenic substrate (e.g., p-nitrophenyl-.beta.-D-galactosidase) or fluorogenic substrate 4-methylumbelliferyl-.beta.-D-galactosidase.

The detectable label can be indirectly conjugated with the antibody. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

Additionally, the antibody of the invention need not be labeled, and the presence thereof can be detected using a labeled antibody which binds to the antibody of the invention.

For immunohistochemistry, a tissue sample may be fresh or frozen or may be embedded in paraffin and fixed with a preservative such as formalin.

The antibodies may also be used for in vivo diagnostic assays. Generally, the antibody is labeled with a radio nuclide (such as $^{111}$In, $^{99}$Tc, $^{14}$C, $^{131}$I, $^{125}$I, $^{3}$H, $^{32}$P or $^{35}$S) so that the Stem Cell Factor can be localized using immunoscintiography.

The antibodies of the invention may be used as affinity purification agents. In this process, the antibodies are immobilized on a solid phase such as glass or plastic slides, tissue culture plates, microtiter wells, tubes, silicon chips, or particles such as beads, using methods well known in the art. The immobilized antibody is contacted with a sample containing the Stem Cell Factor to be purified, and thereafter the support is washed with a suitable solvent that will remove substantially all the material in the sample except Stem Cell Factor protein, which is bound to the immobilized antibody. Finally, the support is washed with another suitable solvent, such as a buffer at a pH that will release the Stem Cell Factor protein from the antibody.

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

All patents and patent applications cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLES

Example 1

Construction of a Human Combinatorial Antibody Library (HuCAL-Fab 1)

1.1 Cloning of HuCAL-Fab 1.

HuCAL-Fab 1 is a fully synthetic, modular human antibody library in the Fab antibody fragment format. HuCAL-Fab 1 was assembled starting from an antibody library in the single-chain format (HuCAL-scFv) in accordance with the method of Knappik et al., *J. Mol. Biol.* 296: 55-86 (2000)). The heavy and light chain variable region sequences in the library are shown in Tables 1 and 2.

The sequence identification numbers for Tables 1 and 2 are as follows:

Table 1—VLκ1—SEQ ID NO: 26; VLκ2—SEQ ID NO: 27; VLκ3—SEQ ID NO: 28; VLκ4—SEQ ID NO: 29; VLλ1—SEQ ID NO: 30; VLλ2—SEQ ID NO: 31; VLλ3—SEQ ID NO: 32; VH1A—SEQ ID NO: 33; VH1B—SEQ ID NO: 34; VH2—SEQ ID NO: 35; VH3—SEQ ID NO: 36; VH4—SEQ ID NO: 37; VH5—SEQ ID NO: 38; VH6—SEQ ID NO: 39.

Table 2—VLκ1—SEQ ID NO: 40; VLκ2—SEQ ID NO: 41; VLκ3—SEQ ID NO: 42; VLκ4—SEQ ID NO: 43; VLλ1—SEQ ID NO: 44; VLλ2—SEQ ID NO: 45; VLλ3—SEQ ID NO: 46; VH1A—SEQ ID NO: 47; VH1B—SEQ ID NO: 48; VH2—SEQ ID NO: 49; VH3—SEQ ID NO: 50; VH4—SEQ ID NO: 51; VH5—SEQ ID NO: 52; VH6—SEQ ID NO: 53.

TABLE 1

Sequence Summary HuCAL Libraries scFv1, scFv2, scFv3 and Fab1

VL

| | Framework 1 | | | | | | | | | | | | | | | | | | | | | | CDR 1 | | | | | | | | | | |
|---|---|---|---|---|---|---|---|---|---|---|---|---|---|---|---|---|---|---|---|---|---|---|---|---|---|---|---|---|---|---|---|---|---|
| Position | 1 | | | | | | | | | 1 | | | | | | | | | | 2 | | | | 3 | | | | | | | | | |
| | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | a | b | c | d | e | f | 1 | 2 | 3 | 4 |
| | EcoRV | | | | BanII | | | | | | | | | | | | | | | | | | | PstI | | | | | | | | | | |
| VLκ1 | D | I | Q | M | T | Q | S | P | S | S | L | S | A | S | V | G | D | R | V | T | I | T | C | R | A | S | Q | G | I | S | · | · | · | · | · | · | S | Y | L | A |
| VLκ2 | D | I | V | M | T | Q | S | P | L | S | L | P | V | T | P | G | E | P | A | S | I | S | C | R | S | S | Q | S | L | L | H | S | · | N | G | Y | N | Y | L | D |
| VLκ3 | D | I | V | L | T | Q | S | P | A | T | L | S | L | S | P | G | E | R | A | T | L | S | C | R | A | S | Q | S | V | S | S | · | · | · | · | · | S | Y | L | A |
| VLκ4 | D | I | V | M | T | Q | S | P | D | S | L | A | V | S | L | G | E | R | A | T | I | N | C | R | S | S | Q | S | V | L | Y | S | S | N | N | K | N | Y | L | A |
| VLλ1 | D | I | V | L | T | Q | P | P | · | S | V | S | G | A | P | G | Q | R | V | T | I | S | C | S | G | S | S | S | N | I | G | S | · | · | · | · | N | Y | V | S |
| VLλ2 | D | I | A | L | T | Q | P | A | · | S | V | S | G | S | P | G | Q | S | I | T | I | S | C | T | G | T | S | S | D | V | G | G | Y | · | · | · | N | Y | V | S |
| VLλ3 | D | I | E | L | T | Q | P | P | · | S | V | S | V | A | P | G | Q | T | A | R | I | S | C | S | G | D | A | L | G | D | · | · | · | · | · | · | K | Y | A | S |
| | EcoRV | | | | | | | | | | | | | | SexAI | | | | | | | | BssSI | | | | | | | | | | | |

| | Framework 2 | | | | | | | | | | CDR 2 | | | | | | | | Framework 3 | | | | | | | | | | | |
|---|---|---|---|---|---|---|---|---|---|---|---|---|---|---|---|---|---|---|---|---|---|---|---|---|---|---|---|---|---|---|
| | | | | | 4 | | | | | | | 5 | | | | | | | | 6 | | | | | | | | 7 | | | |
| | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 |
| | KpnI | | | | SexAI | | | | | | AseI | | | | | | | | | | SanDI | | | | | | | BamHI | | |
| | W | Y | Q | Q | K | P | G | K | A | P | K | L | L | I | Y | A | A | S | S | L | Q | S | G | V | P | S | R | F | S | G | S | G | S | G | T | D | F | T | L | T |
| | W | Y | L | Q | K | P | G | Q | S | P | Q | L | L | I | Y | L | E | S | N | R | A | S | G | V | P | D | R | F | S | G | S | G | S | G | T | D | F | T | L | K |
| | W | Y | Q | Q | K | P | G | Q | A | P | R | L | L | I | Y | G | A | S | S | R | A | T | G | V | P | A | R | F | S | G | S | G | S | G | T | D | F | T | L | T |
| | W | Y | Q | Q | K | P | G | Q | P | P | K | L | L | I | Y | W | A | S | A | R | E | S | G | V | P | D | R | F | S | G | S | G | S | G | T | D | F | T | L | T |
| | W | Y | Q | Q | L | P | G | T | A | P | K | L | L | I | Y | D | N | N | Q | R | P | S | G | V | P | D | R | F | S | G | S | K | S | G | T | S | A | S | L | A |
| | W | Y | Q | Q | H | P | G | K | A | P | K | L | M | I | Y | D | V | S | N | R | P | S | G | V | S | N | R | F | S | G | S | K | S | G | N | T | A | S | L | T |
| | W | Y | Q | Q | K | P | G | Q | A | P | V | L | V | I | Y | D | D | S | D | R | P | S | G | I | P | E | R | F | S | G | S | N | S | G | N | T | A | T | L | T |
| | KpnI | | | | XmaI | | | BbeI | | | | | | | | | | | | Bsu36I | | | | | | | BamHI | | | |

| | Framework 3 | | | | | | | | | | CDR 3 | | | | | | | | | | | Framework 4 | | | | | | | | |
|---|---|---|---|---|---|---|---|---|---|---|---|---|---|---|---|---|---|---|---|---|---|---|---|---|---|---|---|---|---|---|
| | | | | | 8 | | | | | | | 9 | | | | | | | | | | 10 | | | | | | | | |
| | 5 | 6 | 7 | 8 | 9 | 0 | 1 | 2 | 3 | 4 | 5 | 6 | 7 | 8 | 9 | 0 | 1 | 2 | 3 | 4 | 5 | a | b | 6 | 7 | 8 | 9 | 0 | 1 | 2 | 3 | 4 | 5 | 6 | 7 | 8 | 9 |
| | | | | | | | BbsI | | | | | | | | | | | | | | | | | | | | | MscI | | | | | | | BsiWI | |
| | I | S | S | L | Q | P | E | D | F | A | T/V | Y | Y | C | x | Q | x | x | x | x | x | - | - | x | T | F | G | Q | G | T | K | V | E | I | K | R | T |
| | I | S | R | V | E | A | E | D | V | G | V | Y | Y | C | x | Q | x | x | x | x | x | - | - | x | T | F | G | Q | G | T | K | V | E | I | K | R | T |
| | I | S | S | L | E | P | E | D | F | A | T/V | Y | Y | C | x | Q | x | x | x | x | x | - | - | x | T | F | G | Q | G | T | K | V | E | I | K | R | T |
| | I | S | S | L | Q | A | E | D | V | A | V | Y | Y | C | x | Q | x | x | x | x | x | - | - | x | T | F | G | Q | G | T | K | V | E | I | K | R | T |
| | I | T | G | L | Q | S | E | D | E | A | D | Y | Y | C | Q | S | x | D | x | x | x | (x) | (x) | x | V | F | G | G | G | T | K | L | T | V | L | G | |
| | I | S | G | L | Q | A | E | D | E | A | D | Y | Y | C | Q | S | x | D | x | x | x | (x) | (x) | x | V | F | G | G | G | T | K | L | T | V | L | G | |
| | I | S | G | T | Q | A | E | D | E | A | D | Y | Y | C | Q | S | x | D | x | x | x | (x) | (x) | x | V | F | G | G | G | T | K | L | T | V | L | G | |
| | | | | | | | BbsI | | | | | | | | | | | | | | | | | | | | | HpaI | | | | | | | MscI | |

VH

TABLE 1-continued

Sequence Summary HuCAL Libraries scFv1, scFv2, scFv3 and Fab1

Framework 1 / CDR 1

Position:
1 2 3 4 5 6 7 8 9 10 11 12 13 14 15 16 17 18 19 20 21 22 23 24 25 26 27 28 29 30 31 31a 31b 32 33 34 35 36 37 38

| | | | MfeI | | | | | | | | | | | | | | | | | | | | | | | BspEI | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|
| VH1A | Q | V | Q L | V | Q | S | G | A | E | V | K | K | P | G | S | S | V | K | V | S | C | K | A | S | G | G | T | F | S | S | · | · | Y | A | I | S | W | V | R |
| VH1B | Q | V | Q L | V | Q | S | G | A | E | V | K | K | P | G | A | S | V | K | V | S | C | K | A | S | G | Y | T | F | T | S | · | · | Y | Y | M | H | W | V | R |
| VH2 | Q | V | Q L | K | E | S | G | P | A | L | V | K | P | T | Q | T | L | T | L | T | C | T | F | S | G | F | S | L | S | T | S | G | V | G | V | G | W | I | R |
| VH3 | Q | V | Q L | V | E | S | P | G | G | L | V | Q | P | G | G | S | L | R | L | S | C | A | A | S | G | F | T | F | S | S | · | · | Y | A | M | S | W | V | R |
| VH4 | Q | V | Q L | Q | E | S | G | P | G | V | V | K | P | S | E | T | L | S | L | I | C | T | V | S | G | G | S | I | S | S | · | · | Y | Y | W | S | W | I | R |
| VH5 | Q | V | Q L | V | Q | S | G | A | E | V | K | K | P | G | E | S | L | K | I | S | C | K | G | S | G | Y | S | F | T | S | · | · | Y | W | I | G | W | V | R |
| VH6 | Q | V | Q L | Q | Q | S | G | P | G | L | V | K | P | S | Q | T | L | S | L | T | C | A | I | S | G | D | S | V | S | S | N | S | A | A | W | N | W | I | R |

Framework 2 / CDR 2 / Framework 3

Position: 49 50 51 52 53 54 55 56 57 58 59 60 61 62a b c 63 64 65 66 67 68 69 70 71 72 73 74

| | BstXI | | | | XhoI | | | | | | | | | | | | | | | | | | | | | | | BstEII | | | NspV |
|---|---|---|---|---|---|---|---|---|---|---|---|---|---|---|---|---|---|---|---|---|---|---|---|---|---|---|---|---|---|---|---|
| Q | A | P | G | Q | G | L | E | W | M | G | G | I | I | P | - | - | I | F | G | T | A | N | Y | A | Q | K | F | Q | G | R | V T | I T A D E S |
| Q | A | P | G | Q | G | L | E | W | M | G | W | I | N | P | - | - | N | S | G | G | T | N | Y | A | Q | K | F | Q | G | R | V T | M T R D T S |
| Q | P | P | G | K | A | L | E | W | L | A | L | I | D | - | - | - | W | D | D | D | K | Y | Y | S | T | S | L | K | T | R | L T | I S K D T S |
| Q | A | P | G | K | G | L | E | W | V | S | A | I | S | G | - | - | S | G | G | S | T | Y | Y | A | D | S | V | K | G | R | F T | I S R D N S |
| Q | P | P | G | K | G | L | E | W | I | G | Y | I | Y | - | - | - | Y | S | G | S | T | N | Y | N | P | S | L | K | S | R | V T | I S V D T S |
| Q | M | P | G | K | G | L | E | W | M | G | I | I | Y | P | - | - | G | D | S | D | T | R | Y | S | P | S | F | Q | G | Q | V T | I S A D K S |
| Q | S | P | G | R | G | L | E | W | L | G | R | T | Y | Y | R | - | S | K | W | Y | N | D | Y | A | V | S | V | K | S | R | I T | I N P D T S |

Framework 3 / CDR 2

Position: 75 76 77 78 79 80 81 82a b c 83 84 85 86 87 88 89 90 91 92 93 94 95 96 97 98 99 100 100a b c d e f g h i j 101 102

| NspV | | | | | | | | | | | | | | | | | | EagI | | | BssHII | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| T | S | T | A | Y | M | E | L | S | S | L | R | S | E | D | T A V | Y | Y | C | A | R | x (x)(x)(x)(x)(x)(x)(x)(x)(x)(x)(x)(x) x x D x |
| I | S | T | A | Y | M | E | L | S | S | L | R | S | E | D | T A V | Y | Y | C | A | R | x (x)(x)(x)(x)(x)(x)(x)(x)(x)(x)(x)(x) x x D x |
| K | N | Q | V | V | L | T | M | T | N | M | D | P | V | D | T A T | Y | Y | C | A | R | x (x)(x)(x)(x)(x)(x)(x)(x)(x)(x)(x)(x) x x D x |
| K | N | T | L | Y | L | Q | M | N | S | L | R | A | E | D | T A V | Y | Y | C | A | R | x (x)(x)(x)(x)(x)(x)(x)(x)(x)(x)(x)(x) x x D x |
| K | N | Q | F | S | L | K | L | S | S | V | T | A | A | D | T A V | Y | Y | C | A | R | x (x)(x)(x)(x)(x)(x)(x)(x)(x)(x)(x)(x) x x D x |
| I | S | T | A | Y | L | Q | W | S | S | L | K | A | S | D | T A M | Y | Y | C | A | R | x (x)(x)(x)(x)(x)(x)(x)(x)(x)(x)(x)(x) x x D x |
| K | N | Q | F | S | L | Q | L | N | S | V | T | P | E | D | T A V | Y | Y | C | A | R | x (x)(x)(x)(x)(x)(x)(x)(x)(x)(x)(x)(x) x x D x |

Framework 4

Position: 103 104 105 106 107 108 109 110 111 112 113

| | | StyI | | | | | | | BlpI | |
|---|---|---|---|---|---|---|---|---|---|---|
| W | G | Q G | T | L | V | T | V | S S |
| W | G | Q G | T | L | V | T | V | S S |
| W | G | Q G | T | L | V | T | V | S S |
| W | G | Q G | T | L | V | T | V | S S |
| W | G | Q D | T | L | V | T | V | S S |
| W | G | Q G | T | L | V | T | V | S S |
| W | G | Q G | T | L | V | T | V | S S |

TABLE 2

Sequence Summary HuCAL Libraries scFv1, scFv2, scFv3 and Fab1

VL

| | | | | | | | | | Framework 1 | | | | | | | | | | |
|---|---|---|---|---|---|---|---|---|---|---|---|---|---|---|---|---|---|---|---|
| Position | 1 | 2 | 3 | 4 | 5 | 6 | 7 | 8 | 9 | 10 | 1 | 2 | 3 | 4 | 5 | 6 | 7 | 8 | 9 | 20 |
| | EcoRV | | | | | | BanII | | | | | | | | | | | | | |
| VLκ1 | GAT | ATC | CAG | ATG | ACC | CAG | AGC | CCG | TCT | AGC | CTG | AGC | GCG | AGC | GTG | GGT | GAT | CGT | GTG | ACC |
| VLκ2 | GAT | ATC | GTG | ATG | ACC | CAG | AGC | CCA | CTG | AGC | CTG | CCA | GTG | ACT | CCG | GGC | GAG | CCT | GCG | AGC |
| VLκ3 | GAT | ATC | GTG | CTG | ACC | CAG | AGC | CCG | GCG | ACC | CTG | AGC | CTG | TCT | CCG | GGC | GAA | CGT | GCG | ACC |
| VLκ4 | GAT | ATC | GTG | ATG | ACC | CAG | AGC | CCG | GAT | AGC | CTG | GCG | GTG | AGC | CTG | GGC | GAA | CGT | GCG | ACC |
| VLλ1 | GAT | ATC | GTG | CTG | ACC | CAG | CCG | CCT | - | TCA | GTG | AGT | GGC | GCA | CCA | GGT | CAG | CGT | GTG | ACC |
| VLλ2 | GAT | ATC | GCA | CTG | ACC | CAG | CCA | GCT | - | TCA | GTG | AGC | GGC | TCA | CCA | GGT | CAG | AGC | ATT | ACC |
| VLλ3 | GAT | ATC | GAA | CTG | ACC | CAG | CCG | CCT | - | TCA | GTG | AGC | GTT | GCA | CCA | GGT | CAG | ACC | GCG | CGT |
| | EcoRV | | | | | | | | | | | | | SexAI | | | | | | |

| Framework 1 | | | | | | | | | CDR 1 | | | | | | | | | |
|---|---|---|---|---|---|---|---|---|---|---|---|---|---|---|---|---|---|---|
| 1 | 2 | 3 | 4 | 5 | 6 | 7 | 8 | 9 | 30 | a | b | c | d | e | f | 1 | 2 | 3 | 4 |
| | | PstI | | | | | | | | | | | | | | | | | |
| ATT | ACC | TGC | AGA | GCG | AGC | CAG | GGC | ATT | AGC | AGC | - | - | - | - | - | - | TAT | CTG | GCG |
| ATT | AGC | TGC | AGA | AGC | AGC | CAA | AGC | CTG | CTG | CAT | AGC | - | AAC | GGC | TAT | AAC | TAT | CTG | GAT |
| CTG | AGC | TGC | AGA | GCG | AGC | CAG | AGC | GTG | AGC | AGC | - | - | - | - | - | AGC | TAT | CTG | GCG |
| ATT | AAC | TGC | AGA | AGC | AGC | CAG | AGC | GTG | CTG | TAT | AGC | AGC | AAC | AAC | AAA | AAC | TAT | CTG | GCG |
| ATC | TCG | TGT | AGC | GGC | AGC | AGC | AGC | ACC | AAT | GGC | AGC | AAC | - | - | - | - | TAT | GTG | AGC |
| ATC | TCG | TGT | ACG | GGT | ACT | AGC | AGC | GAT | GTG | GGC | GGC | GGC | AAC | - | - | - | TAT | ATT | AGC |
| ATC | TCG | TGT | AGC | GGC | - | GAT | GCG | - | CTG | GGC | GAT | GAT | - | - | - | - | TAT | GCG | AGC |
| | | BssSI | | | | | | | | | | | | | | | | | |

| | | | | | | Framework 2 | | | | | | | | CDR 2 | | | | | |
|---|---|---|---|---|---|---|---|---|---|---|---|---|---|---|---|---|---|---|---|
| 5 | 6 | 7 | 8 | 9 | 40 | 1 | 2 | 3 | 4 | 5 | 6 | 7 | 8 | 9 | 50 | 1 | 2 | 3 | 4 |
| | KpnI | | | | SexAI | | | | | | AseI | | | | | | | | |
| TGG | TAC | CAG | CAG | AAA | CCA | GGT | AAA | GCA | CCG | AAA | CTA | TAA | ATT | TAT | GCA | GCC | AGC | AGC | TTG |
| TGG | TAC | CTT | CAA | AAA | CCA | GGT | CAA | AGC | CCG | CAG | CTA | TAA | ATT | TAT | CTG | GGC | AGC | AAC | CGT |
| TGG | TAC | CAG | CAG | AAA | CCA | GGT | CAA | GCA | CCG | CGT | CTA | TTA | ATT | TAT | GGC | GCG | AGC | AGC | CGT |
| TGG | TAC | CAG | CAG | AAA | CCA | GGT | CAG | CCG | CCG | AAA | CTA | TTA | ATT | TAT | TGG | GCA | TCC | ACC | CGT |
| TGG | TAC | CAG | CAG | TTG | CCC | GGG | ACG | GCG | CCG | AAA | CTG | CTG | ATT | TAT | GAT | AAC | AAC | CAG | CGT |
| TGG | TAC | CAG | CAG | CAT | CCC | GGG | AAG | GCG | CCG | AAA | CTG | ATG | ATT | TAT | GAT | GTG | AGC | AAC | CGT |
| TGG | TAC | CAG | CAG | AAA | CCC | GGG | CAG | GCG | CCA | GTT | CTG | GTG | ATT | TAT | GAT | GAT | TCT | GAC | CGT |
| | KpnI | | | | XmaI | | | BbeI | | | | | | | | | | | |

TABLE 2-continued

Sequence Summary HuCAL Libraries scFv1, scFv2, scFv3 and Fab1

| CDR 2 | | | | | Framework 3 | | | | | | | | | | | | | | |
|---|---|---|---|---|---|---|---|---|---|---|---|---|---|---|---|---|---|---|---|
| 5 | 6 | 7 | 8 | 9 | 60 | 1 | 2 | 3 | 4 | 5 | 6 | 7 | 8 | 9 | 70 | 1 | 2 | 3 | 4 |
| | | | SanDI | | | | | | | | | BamHI | | | | | | | |
| CAA | AGC | GGG | GTC | CCG | TCC | CGT | TTT | AGC | GGC | TCT | GGA | TCC | GGC | ACT | GAT | TTT | ACC | CTG | ACC |
| GCC | AGT | GGG | GTC | CCG | GAT | CGT | TTT | AGC | GGC | TCT | GGA | TCC | GGC | ACC | GAT | TTT | ACC | CTG | AAA |
| GCA | ACT | GGG | GTC | CCG | GCG | CGT | TTT | AGC | GGC | TCT | GGA | TCC | GGC | ACG | GAT | TTT | ACC | CTG | ACC |
| GAA | AGC | GGG | GTC | CCG | GAT | CGT | TTT | AGC | GGC | TCT | GGA | TCC | GGC | ACT | GAT | TTT | ACC | CTG | ACC |
| CCC | TCA | GGC | GTG | CCG | GAT | CGT | TTT | AGC | GGA | TCC | AAA | AGC | GGC | ACC | AGC | GCG | AGC | CTT | GCG |
| CCC | TCA | GGC | GTG | AGC | AAC | CGT | TTT | AGC | GGA | TCC | AAA | AGC | GGC | AAC | ACC | GCG | AGC | CTG | ACC |
| CCC | TCA | GGC | ATC | CCG | GAA | CGC | TTT | AGC | GGA | TCC | AAC | AGC | GGC | AAC | ACC | GCG | ACC | CTG | ACC |
| Bsu36I | | | | | | | | | BamHI | | | | | | | | | | |

| Framework 3 | | | | | | | | | | | | | | | CDR 3 | | | | |
|---|---|---|---|---|---|---|---|---|---|---|---|---|---|---|---|---|---|---|---|
| 5 | 6 | 7 | 8 | 9 | 80 | 1 | 2 | 3 | 4 | 5 | 6 | 7 | 8 | 9 | 90 | 1 | 2 | 3 | 4 |
| | | | | | BbsI | | | | | | | | | | | | | | |
| ATT | AGC | AGC | CTG | CAA | CCT | GAA | GAC | TTT | GCG | ACT/GTT | TAT | TAT | TGC | x | CAG | x | x | x | x |
| ATT | AGC | CGT | GTG | GAA | GCT | GAA | GAC | GTG | GGC | GTG | TAT | TAT | TGC | x | CAG | x | x | x | x |
| ATT | AGC | AGC | CTG | GAA | CCT | GAA | GAC | TTT | GCG | ACT/GTT | TAT | TAT | TGC | x | CAG | x | x | x | x |
| ATT | TCG | TCC | CTG | CAA | GCT | GAA | GAC | GTG | GCG | GTG | TAT | TAT | TGC | x | CAG | x | x | x | x |
| ATT | ACG | GGC | CTG | CAA | AGC | GAA | GAC | GAA | GCG | GAT | TAT | TAT | TGC | CAG | TCT | x | GAT | x | x |
| ATT | AGC | GGC | CTG | CAA | GCG | GAA | GAC | GAA | GCG | GAT | TAT | TAT | TGC | CAG | TCT | x | GAT | x | x |
| ATT | AGC | GGC | ACT | CAG | GCG | GAA | GAC | GAA | GCG | GAT | TAT | TAT | TGC | CAG | TCT | x | GAT | x | x |
| | | | | | BbsI | | | | | | | | | | | | | | |

| CDR 3 | | | | Framework 4 | | | | | | | | | | | |
|---|---|---|---|---|---|---|---|---|---|---|---|---|---|---|---|
| 5 | a | b | 6 | 7 | 8 | 9 | 100 | 1 | 2 | 3 | 4 | 5 | 6 | 7 | 8 | 9 |
| | | | | | MscI | | | | | | | | | | BsiWI | |
| x | - | - | x | ACC | TTT | GGC | CAG | GGT | ACG | AAA | GTT | GAA | ATT | AAA | CGT | ACG |
| x | - | - | x | ACC | TTT | GGC | CAG | GGT | ACG | AAA | GTT | GAA | ATT | AAA | CGT | ACG |
| x | - | - | x | ACC | TTT | GGC | CAG | GGT | ACG | AAA | GTT | GAA | ATT | AAA | CGT | ACG |
| x | - | - | x | ACC | TTT | GGC | CAG | GGT | ACG | AAA | GTT | GAA | ATT | AAA | CGT | ACG |
| x | (x) | (x) | x | GTG | TTT | GGC | GGC | GGC | ACG | AAG | TTA | ACC | GTT | CTT | GGC | CAG |
| x | (x) | (x) | x | GTG | TTT | GGC | GGC | GGC | ACG | AAG | TTA | ACC | GTT | CTT | GGC | CAG |
| x | (x) | (x) | x | GTG | TTT | GGC | GGC | GGC | ACG | AAG | TTA | ACC | GTT | CTT | GGC | CAG |
| | | | | | | | | | | HpaI | | | | MscI | | |

VH

TABLE 2-continued

Sequence Summary HuCAL Libraries scFv1, scFv2, scFv3 and Fab1

| | Framework 1 | | | | | | | | | | | | | | | | | | | |
|---|---|---|---|---|---|---|---|---|---|---|---|---|---|---|---|---|---|---|---|---|
| Position | 1 | 2 | 3 | 4 | 5 | 6 | 7 | 8 | 9 | 10 | 11 | 12 | 13 | 14 | 15 | 16 | 17 | 18 | 19 | 20 |
| | | | | MfeI | | | | | | | | | | | | | | | | |
| VH1A | CAG | GTG | CAA | TTG | GTT | CAG | TCT | GGC | GCG | GAA | GTG | AAA | AAA | CCG | GGC | AGC | AGC | GTG | AAA | GTG |
| VH1B | CAG | GTG | CAA | TTG | GTT | CAG | AGC | GGC | GCG | GAA | GTG | AAA | AAA | CCG | GGC | GCG | AGC | GTG | AAA | GTG |
| VH2 | CAG | GTG | CAA | TTG | AAA | GAA | AGC | GGC | CCG | GCC | CTG | GTG | AAA | CCG | ACC | CAA | ACC | CTG | ACC | CTG |
| VH3 | CAG | GTG | CAA | TTG | GTG | GAA | AGC | GGC | GGC | GGC | CTG | GTG | CAA | CCG | GGC | GGC | AGC | CTG | CGT | CTG |
| VH4 | CAG | GTG | CAA | TTG | CAA | GAA | AGT | GGC | CCG | GGC | CTG | GTG | AAA | CCG | AGC | GAA | ACC | CTG | AGC | CTG |
| VH5 | CAG | GTG | CAA | TTG | GTT | CAG | AGC | GGC | GCG | GAA | GTG | AAA | AAA | CCG | GGC | GAA | AGC | CTG | AAA | ATT |
| VH6 | CAG | GTG | CAA | TTG | CAA | CAG | TCT | GGT | GGT | GGC | CTG | GTG | AAA | CCG | AGC | CAA | ACC | CTG | AGC | CTG |

| | Framework 1 | | | | CDR 1 | | | | | | | | | | Framework 2 | |
|---|---|---|---|---|---|---|---|---|---|---|---|---|---|---|---|---|
| 1 | 2 | 3 | 4 | 5 | 6 | 7 | 8 | 9 | 30 | 1 | a | b | 2 | 3 | 4 | 5 | 6 | 7 |
| | | | | | BspEI | | | | | | | | | | | | | |
| AGC | TGC | AAA | GCC | TCC | GGA | GGC | ACT | TTT | AGC | AGC | - | - | TAT | GCG | ATT | AGC | TGG | GTG |
| AGC | TGC | AAA | GCC | TCC | GGA | TAT | ACC | TTT | ACC | AGC | - | - | TAT | TAT | ATG | CAC | TGG | GTC |
| ACC | TGT | ACC | TT | TCC | GGA | TTT | AGC | CTG | TCC | ACG | TCT | GGC | GTT | GGC | GTG | GGC | TGG | ATT |
| AGC | TGC | GCG | GCC | TCC | GGA | TTT | ACC | TTT | AGC | AGC | - | - | TAT | GCG | ATG | AGC | TGG | GTG |
| ACC | TGC | ACC | GTT | TCC | GGA | GGC | AGC | ATT | AGC | AGC | - | - | TAT | TAT | TGG | AGC | TGG | ATT |
| AGC | TGC | AAA | GGT | TCC | GGA | TAT | TCC | TTT | ACG | AGC | - | - | TAT | TGG | ATT | GGC | TGG | GTG |
| ACC | TGT | GCG | ATT | TCC | GGA | GAT | AGC | GTG | AGC | AGC | AAC | AGC | GCG | GCG | TGG | AAC | TGG | ATT |

| | Framework 2 | | | | | | | | | CDR 2 | | | | | | |
|---|---|---|---|---|---|---|---|---|---|---|---|---|---|---|---|---|
| 8 | 9 | 40 | 1 | 2 | 3 | 4 | 5 | 6 | 7 | 8 | 9 | 50 | 1 | 2 | a | b | c | 3 | 4 |
| | BstXI | | | | | XhoI | | | | | | | | | | | | | |
| CGC | CAA | GCC | CCT | GGG | CAG | GGT | CTC | GAG | TGG | ATG | GGC | GGC | ATT | ATT | CCG | - | - | ATT | TTT |
| CGC | CAA | GCC | CCT | GGG | CAG | GGT | CTC | GAG | TGG | ATG | GGC | TGG | ATT | AAC | CCG | - | - | AAT | AGC |
| CGC | CAG | CCG | CCT | GGG | AAA | GCC | CTC | GAG | TGG | CTG | GCT | CTG | ATT | GAT | - | - | TGG | GAT |
| CGC | CAA | GCC | CCT | GGG | AAG | GGT | CTC | GAG | TGG | GTG | AGC | GCG | ATT | AGC | GGT | - | - | AGC | GGC |
| CGC | CAG | CCG | CCT | GGG | AAG | GGT | CTC | GAG | TGG | ATT | GGC | TAT | ATT | TAT | - | - | TAT | AGC |
| CGC | CAG | ATG | CCT | GGG | AAG | GGT | CTC | GAG | TGG | ATG | GGC | ATT | ATT | TAT | CCG | - | - | GGC | GAT |
| CGC | CAG | TCT | CCT | GGG | CGT | GGC | CTC | GAG | TGG | CTG | GGC | CGT | ACC | TAT | TAT | CGT | - | AGC | AAA |

| | CDR 2 | | | | | | | | | | Framework 3 | | | | | |
|---|---|---|---|---|---|---|---|---|---|---|---|---|---|---|---|---|
| 5 | 6 | 7 | 8 | 9 | 60 | 1 | 2 | 3 | 4 | 5 | 6 | 7 | 8 | 9 | 70 | 1 | 2 | 3 | 4 |
| | | | | | | | | | | | | BstEII | | | | | | | NspV |
| GGC | ACG | GCG | AAC | TAC | GCG | CAG | AAG | TTT | CAG | GGC | CGG | GTG | ACC | ATT | ACC | GCG | GAT | GAA | AGC |
| GGC | GGC | ACG | AAC | TAC | GCG | CAG | AAG | TTT | CAG | GGC | CGG | GTG | ACC | ATG | ACC | CGT | GAT | ACC | AGC |
| GAT | GAT | AAG | TAT | TAT | AGC | ACC | AGC | CTG | AAA | ACG | CGT | CTG | ACC | ATT | AGC | AAA | GAT | ACT | TCG |
| GGC | AGC | ACC | TAT | TAT | GCG | GAT | AGC | GTG | AAA | GGC | CGT | TTT | ACC | ATT | TCA | CGT | GAT | AAT | TCG |
| GGC | AGC | ACC | AAC | TAT | AAT | CCG | AGC | CTG | AAA | AGC | CGG | GTG | ACC | ATT | AGC | GTT | GAT | ACT | TCG |
| AGC | GAT | ACC | CGT | TAT | TCT | CCG | AGC | TTT | CAG | GGC | CAG | GTG | ACC | ATT | AGC | GCG | GAT | AAA | AGC |
| TGG | TAT | AAC | GAT | TAT | GCG | GTG | AGC | GTG | AAA | AGC | CGG | ATT | ACC | ATC | AAC | CCG | GAT | ACT | TCG |

TABLE 2-continued

Sequence Summary HuCAL Libraries scFv1, scFv2, scFv3 and Fab1

Framework 3

```
                            8                                                              9
 5   6   7   8   9   0   1   2   a   b   c   3   4   5   6   7   8   9   0   1
                                                                    EagI
ACC AGC ACC GCG TAT ATG GAA CTG AGC AGC CTG CGT AGC GAA GAT ACG GCC GTG TAT TAT
ATT AGC ACC GCG TAT ATG GAA CTG AGC AGC CTG CGT AGC GAA GAT ACG GCC GTG TAT TAT
AAA AAT CAG GTG GTG CTG ACT ATG ACC AAC ATG GAC CCG GTG GAT ACG GCC ACC TAT TAT
AAA AAC ACC GTG TAT CTG CAA ATG AAC AGC CTG CGT GCG GAA GAT ACG GCC GTG TAT TAT
AAA AAC CAG TTT AGC CTG AAA CTG AGC AGC CTG ACG GCG GCG GAT ACG GCC GTG TAT TAT
ATT AGC ACC GCG TAT CTT CAA TGG AGC AGC CTG AAA GCG AGC GAT ACG GCC ATG TAT TAT
AAA AAC CAG TTT AGC CTG CAA CTG AAC AGC GTG ACC CCG GAA GAT ACG GCC GTG TAT
```

| Framework 3 | CDR 3 | | | | | | | | | | | | | | | | |
|---|---|---|---|---|---|---|---|---|---|---|---|---|---|---|---|---|---|
| 2 3 4 | 5 | 6 | 7 | 8 | 9 | 10 0 | a | b | c | d | e | f | g | h | i | j | 1 2 |
| BssHII | | | | | | | | | | | | | | | | | |
| TGC GCG CGT | x | (x) | (x) | (x) | (x) | (x) | (x) | (x) | (x) | (x) | (x) | (x) | (x) | (x) | x | x | GAT x |
| TGC GCG CGT | x | (x) | (x) | (x) | (x) | (x) | (x) | (x) | (x) | (x) | (x) | (x) | (x) | (x) | x | x | GAT x |
| TGC GCG CGT | x | (x) | (x) | (x) | (x) | (x) | (x) | (x) | (x) | (x) | (x) | (x) | (x) | (x) | x | x | GAT x |
| TGC GCG CGT | x | (x) | (x) | (x) | (x) | (x) | (x) | (x) | (x) | (x) | (x) | (x) | (x) | (x) | x | x | GAT x |
| TGC GCG CGT | x | (x) | (x) | (x) | (x) | (x) | (x) | (x) | (x) | (x) | (x) | (x) | (x) | (x) | x | x | GAT x |
| TGC GCG CGT | x | (x) | (x) | (x) | (x) | (x) | (x) | (x) | (x) | (x) | (x) | (x) | (x) | (x) | x | x | GAT x |
| TGC GCG CGT | x | (x) | (x) | (x) | (x) | (x) | (x) | (x) | (x) | (x) | (x) | (x) | (x) | (x) | x | x | GAT x |

Framework 4

```
                        11
 3   4   5   6   7   8   9   0   1   2   3
        StyI                        BlpI
TGG GGC CAA GGC ACC CTG GTG ACG GTT AGC TCA GC
TGG GGC CAA GGC ACC CTG GTG ACG GTT AGC TCA GC
TGG GGC CAA GGC ACC CTG GTG ACG GTT AGC TCA GC
TGG GGC CAA GGC ACC CTG GTG ACG GTT AGC TCA GC
TGG GGC CAA GGC ACC CTG GTG ACG GTT AGC TCA GC
TGG GGC CAA GGC ACC CTG GTG ACG GTT AGC TCA GC
TGG GGC CAA GGC ACC CTG GTG ACG GTT AGC TCA GC
```

HuCAL-Fab 1 was cloned into a phagemid expression vector pMORPH18 Fab1 (FIG. 1). This vector comprises the Fd fragment with a phoA signal sequence fused at the C-terminus to a truncated gene III protein of filamentous phage, and further comprises the light chain VL-CL with an ompA signal sequence. Both chains are under the control of the lac operon. The constant domains Cλ, Cκ, and CH are synthetic genes fully compatible with the modular system of HuCAL (Knappik et al., 2000).

First, the Vλ and Vκ libraries were isolated from HuCAL-scFv by restriction digest using EcoRV/DraIII and EcoRV/BsiWI, respectively. These Vλ and Vκ libraries were cloned into pMORPH18 Fab 1 cut with EcoRV/DraIII and EcoRV/BsiWI, respectively. After ligation and transformation in *E. coli* TG-1, library sizes of $4.14 \times 10^8$ and $1.6 \times 10^8$, respectively, were obtained, in both cases exceeding the VL diversity of HuCAL-scFv.

Similarly, the VH library was isolated from HuCAL-scFv by restriction digest using StyI/MunI. This VH library was cloned into the pMORPH 18-Vλ and Vκ libraries cut with StyI/MunI. After ligation and transformation in *E. coli* TG-1, a total library size of $2.09 \times 10^{10}$ was obtained, with 67% correct clones (as identified by sequencing of 207 clones).

1.2 Phagemid rescue, phage amplification and purification.

HuCAL-Fab was amplified in 2×TY medium containing 34 μg/ml chloramphenicol and 1% glucose (2×TY-CG). After helper phage infection (VCSM13) at 37° C. at an OD600 of about 0.5, centrifugation and resuspension in 2×TY/34 μg/ml chloramphenicol/50 μg/ml kanamycin, cells were grown overnight at 30° C. Phage were PEG-precipitated from the supernatant (Ausubel et al., 1998), resuspended in PBS/20% glycerol, and stored at −80° C. Phage amplification between two panning rounds was conducted as follows: mid-log phase TG1-cells were infected with eluted phage and plated onto LB-agar supplemented with 1% of glucose and 34 μg/ml of chloramphenicol. After overnight incubation at 30° C., colonies were scraped off and adjusted to an OD600 of 0.5. Helper phage were added as described above.

Example 2

Design of the CDR3 Libraries Vλ Positions 1 and 2.

The original HuCAL master genes (Knappik et al. *J. Mol. Biol.* 296: 55 (2000)) were constructed with their authentic N-termini: VLλ1: QS (CAGAGC), VLλ2: QS (CAGAGC), and VLλ3: SY (AGCTAT). Sequences containing these amino acids are shown in WO 97/08320. During HuCAL library construction, the first two amino acids were changed to DI to facilitate library cloning (EcoRI site). All HuCAL libraries contain VLλ genes with the EcoRV site GATATC (DI) at the 5′-end. All HuCAL kappa genes (master genes and all genes in the library) contain DI at the 5′-end.

VH Position 1.

The original HuCAL master genes were constructed with their authentic N-termini: VH1A, VH1B, VH2, VH4, and VH6 with Q (=CAG) as the first amino acid and VH3 and VH5 with E (=GAA) as the first amino acid. Sequences containing these amino acids are shown in WO 97/08320. In the HuCAL Fab 1 library, all VH chains contain Q (=CAG) at the first position.

Vκ1/Vκ3 Position 85.

Because of the cassette mutagenesis procedure used to introduce the CDR3 library (Knappik et al., *J. Mol. Biol.* 296, 57-86, 2000), position 85 of Vκ1 and Vκ3 can be either T or V. Thus, during HuCAL scFv 1 library construction, position 85 of Vκ1 and Vκ3 was varied as follows: Vκ1 original, 85T (codon ACC); Vκ1 library, 85T or 85V (TRIM codons ACT or GTT); Vκ3 original, 85V (codon GTG); Vκ3 library, 85T or 85V (TRIM codons ACT or GTT); the same applies to HuCAL Fab1.

CDR3 Design.

All CDR3 residues which were kept constant are indicated in TABLE 1.

CDR3 Length.

The designed CDR3 length distribution is as follows. Residues which were varied are shown in brackets (x) in TABLE 1. Vκ CDR3, 8 amino acid residues (position 89 to 96) (occasionally 7 residues), with Q90 fixed; V lambda CDR3, 8 to 10 amino acid residues (position 89 to 96) (occasionally 7-10 residues), with Q89, S90, and D92 fixed; and VH CDR3, 5 to 28 amino acid residues (position 95 to 102) (occasionally 4-28), with D101 fixed.

Example 3

Solid Phase Panning

Wells of MaxiSorp™ microtiter plates (Nunc, Wiesbaden, Germany) were coated with rat- or human TIMP protein dissolved in PBS (2 μg/well). After blocking with 5% non-fat dried milk in PBS, 1-5×1012 HuCAL-Fab phage purified as above were added for 1 h at 20° C. After several washing steps, bound phage were eluted by pH-elution with 100 mM triethylamine and subsequent neutralization with 1M TRIS-Cl pH 7.0. Three rounds of panning were performed with phage amplification conducted between each round as described in Example 1.

Example 4

Subcloning of Selected Fab Fragments for Expression

Figure 2:
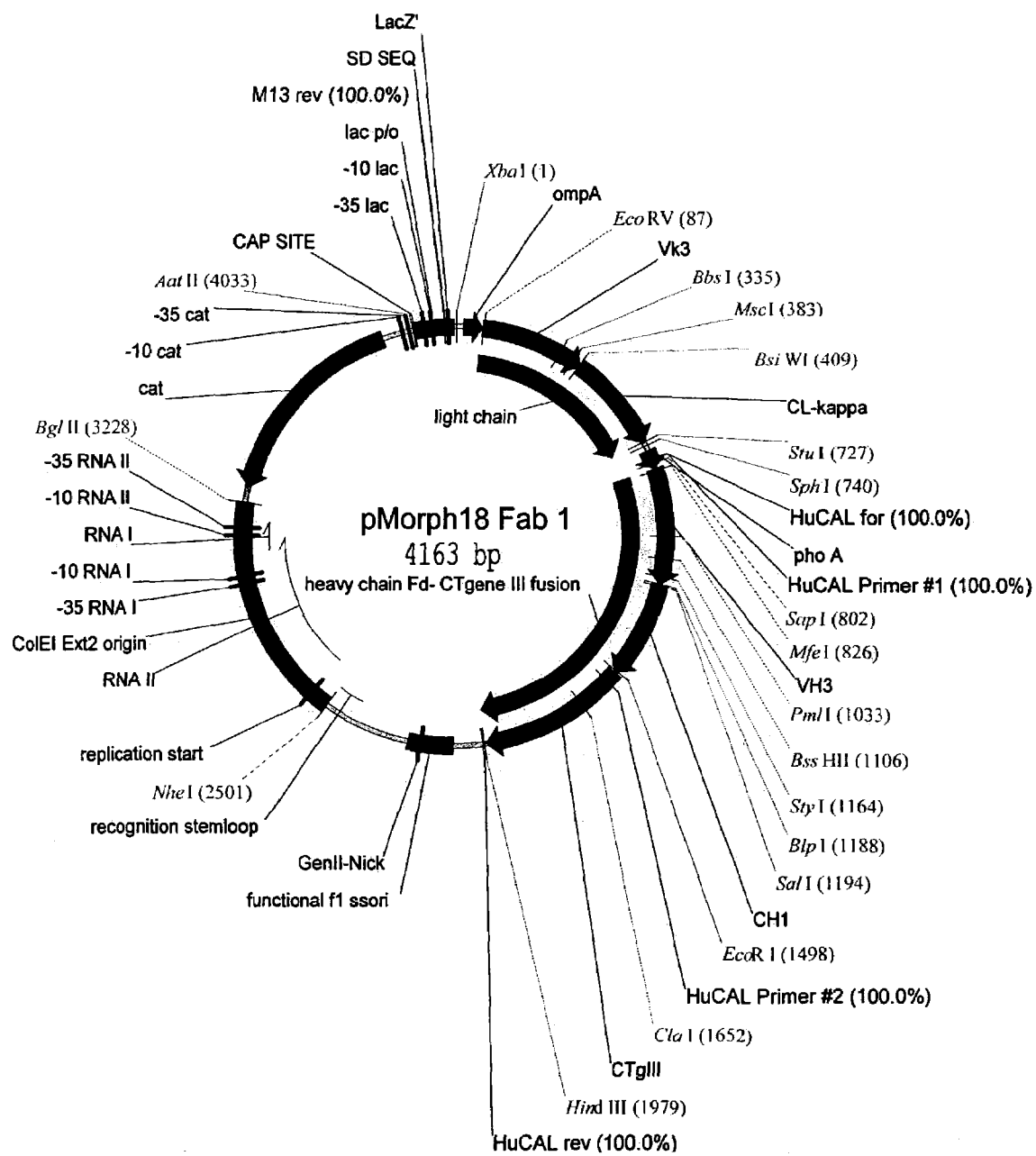
FIG. 2 Fab display vector pMORPH18 Fab 1.

The Fab-encoding inserts of the selected HuCAL Fab fragments were subcloned into the expression vector pMORPHx7_FS to facilitate rapid expression of soluble Fab. The DNA preparation of the selected HuCAL Fab clones was digested with XbaI/EcoRI, thus cutting out the Fab encoding insert (ompA-VL and phoA-Fd). Subcloning of the purified inserts into the XbaI/EcoRI cut vector pMORPHx7, previously carrying a scFv insert, leads to a Fab expression vector designated pMORPHx9_Fab1_FS which is shown in FIG. 2). Fabs expressed in this vector carry two C-terminal tags (FLAG and Strep) for detection and purification.

Example 5

Identification of Stem Cell Factor-Binding Fab Fragments by ELISA

The wells of a Maxisorp ELISA plates were coated with 100 µl/well solutions of rat Stem Cell Factor or human Stem Cell Factor at a concentration of 5 µg/ml diluted in coating buffer. Expression of individual Fab was induced with 0.5 mM IPTG for 12 h at 30° C. Soluble Fab was extracted from the periplasm by osmotic shock (Ausubel et al., 1998) and used in an ELISA. The Fab fragment was detected with an anti-Fab antibody (Dianova, Hamburg, Germany). Values at 370 nm were read out after addition of horseradish peroxidase-conjugated anti-mouse IgG antibody and POD soluble substrate (Roche Diagnostics, Pleasanton, Calif., USA).

TABLE 3

STEM CELL FACTOR ANTIBODY SEQUENCES

| | | Framework + CDR 3 Sequence | | | Affinity $K_D$ | Efficacy |
|---|---|---|---|---|---|---|
| Fab | VH | HCDR3 | VL | VCDR3 | (nM) | $IC_{50}$ (µg/ml) |
| A1 | H3 | GINSRRQRQFDY (SEQ ID NO:13) | Vκ1 | QQYGSIST (SEQ ID NO:19) | 39.6 | 30 |
| A2 | H3 | RDFFAHFDV (SEQ ID NO:14) | Vκ1 | QQYSGMPY (SEQ ID NO:20) | 65.7 | 29 |
| A8 | H3 | GYFDEFDV (SEQ ID NO:15) | Vκ1 | QSRDHYVVRW (SEQ ID NO:24) | 9.7 | 30 |
| D5 | H3 | YSYYFDV (SEQ ID NO:16) | Vκ1 | QQFDMFPD (SEQ ID NO:21) | 29.0 | 12 |
| E6 | H3 | NYSSPFGYMFLISYYAFDN (SEQ ID NO:17) | Vκ1 | QQINSRPP (SEQ ID NO:22) | 27.3 | 10 |
| F8 | H3 | YGYFLYNGDFDN (SEQ ID NO:18) | Vκ1 | QSYDHPLI (SEQ ID NO:23) | 7.1 | n/a |

TABLE 4

| SEQ. I.D. | Framework | |
|---|---|---|
| | | Nucleic Acid Sequences |
| 1 | VH3-CD3 | GGTATTAATTCTCGTCGTCAGCGTCAGTTTGATTAT |
| 2 | VH3-CD3 | CGTGATTTTTTTGCTCACTTTGATGTT |
| 3 | VH3-CD3 | GGTTATTTTGATGAGTTTGATGTT |
| 4 | VH3-CD3 | TATTCTTATTATTTTGATGTT |
| 5 | VH3-CD3 | AATTATTCTTCTCCTTTTGGTTATATGTTTCTTATTTCTTATTAT GCTTTTGATAAT |
| 6 | VH3-CD3 | TATGGTTATTTTCTTTATAATGGTGATTTTGATAAT |
| 7 | VLκ1-CD3 | CAGCAGTATGGTTCTATTTCTACT |
| 8 | VLκ1-CD3 | CAGCAGTATTCTGGTATGCCTTAT |
| 9 | VLκ1-CD3 | CAGCAGTTTGATATGTTTCCTGAT |
| 10 | VLκ1-CD3 | CAGCAGATTAATTCTCGTCCTCCT |
| 11 | VLκ1-CD3 | CAGAGCTATGACCATCCTCTTATT |
| 12 | VLλ1-CD3 | CAGAGCCGTGACCATTATGTTGTTCGTTGG |
| | | Amino Acid Sequences |
| 13 | VH3-CD3 | GINSRRQRQFDY |
| 14 | VH3-CD3 | RDFFAHFDV |
| 15 | VH3-CD3 | GYFDEFDV |
| 16 | VH3-CD3 | YSYYFDV |
| 17 | VH3-CD3 | NYSSPFGYMFLISYYAFDN |
| 18 | VH3-CD3 | YGYFLYNGDFDN |
| 19 | VLκ1-CD3 | QQYGSIST |
| 20 | VLκ1-CD3 | QQYSGMPY |
| 21 | VLκ1-CD3 | QQFDMFPD |
| 22 | VLκ1-CD3 | QQINSRPP |
| 23 | VLκ1-CD3 | QSYDHPLI |
| 24 | VLλ1-CD3 | QSRDHYVVRW |
| 25 | Stem Cell Factor | MEGICRNRVTNNVKDVTKLVANLPKDYMITLKYVPGMDVLPSHCW ISEMVVQLSDSLTDLLDKFSNISEGLSNYSHDKLVNIVDDLVECV KENSSKDLKKSFKSPEPRLFTPEEFFRIFNRSIDAFKDFVVASET SDCVVSSTLSPEKDSRVSVTKPFMLPPVA |

Kappa light chain constant region (DNA sequence):

(SEQ ID NO: 82)
GTGGCTGCACCATCTGTCTTCATCTTCCCGCCATCTGATGAGCAGTTGAA

ATCTGGAACTGCCTCTGTTGTGTGCCTGCTGAATAACTTCTATCCCAGAG

AGGCCAAAGTACAGTGGAAGGTGGATAACGCCCTCCAATCGGGTAACTCC

CAGGAGAGTGTCACAGAGCAGGACAGCAAGGACAGCACCTACAGCCTCAG

CAGCACCCTGACGCTGAGCAAAGCAGACTACGAGAAACACAAAGTCTACG

CCTGCGAAGTCACCCATCAGGGCCTGAGCTCGCCCGTCACAAAGAGCTTC

AACAGGGGAGAGTGTTAG

Kappa light chain constant region (protein sequence):

(SEQ ID NO: 83)
VAAPSVFIFPPSDEQLKSGTASVVCLLNNFYPREAKVQWKVDNALQSGNS
QESVTEQDSKDSTYSLSSTLTLSKADYEKHKVYACEVTHQGLSSPV
TKSFNRGEC

Lambda light chain constant region (DNA sequence):

(SEQ ID NO: 84)
ACCGTCCTAGGTCAGCCCAAGGCTGCCCCCTCGGTCACTCTGTTCCCGCC

CTCCTCTGAGGAGCTTCAAGCCAACAAGGCCACACTGGTGTGTCTCATAA

GTGACTTCTACCCGGGAGCCGTGACAGTGGCCTGGAAGGGAGATAGCAGC

CCCGTCAAGGCGGGAGTGGAGACCACCACACCCTCCAAACAAAGCAACAA

CAAGTACGCGGCCAGCAGCTATCTGAGCCTGACGCCTGAGCAGTGGAAGT

CCCACAGAAGCTACAGCTGCCAGGTCACGCATGAAGGGAGCACCGTGGAG

AAGACAGTGGCCCCTACAGAATGTTCATAG

Lambda light chain constant region (protein sequence):

(SEQ ID NO: 85)
TVLGQPKAAPSVTLFPPSSEELQANKATLVCLISDFYPGAVTVAWKGDSS
PVKAGVETTTPSKQSNNKYAASSYLSLTPEQWKSHRSYSCQVTHEGSTVE
KTVAPTECS

Example 6

Construction of HuCAL Immunoglobulin Expression Vectors

Heavy chain cloning.

The multiple cloning site of pcDNA3.1+ (Invitrogen, Carlsbad, Calif., USA) was removed (NheI/ApaI), and a stuffer compatible with the restriction sites used for HuCAL design was inserted for the ligation of the leader sequences (NheI/EcoRI), VH-domains (EcoRI/BlpI), and the immunoglobulin constant regions (BlpI/ApaI). The leader sequence (EMBL M83133) was equipped with a Kozak sequence (Kozak, 1987). The constant regions of human IgG1 (PIR J00228), IgG4 (EMBL K01316), and serum IgA1 (EMBL J00220) were dissected into overlapping oligonucleotides with lengths of about 70 bases. Silent mutations were introduced to remove restriction sites non-compatible with the HuCAL design. The oligonucleotides were spliced by overlap extension-PCR.

Light Chain Cloning.

The multiple cloning site of pcDNA3.1/Zeo+ (Invitrogen, Carlsbad, Calif., USA) was replaced by two different stuffers. The κ-stuffer provided restriction sites for insertion of a κ-leader (NheI/EcoRV), HuCAL-scFv Vk-domains (EcoRV/BsiWI,) and the κ-chain constant region (BsiWI/ApaI). The corresponding restriction sites in the λ-stuffer were NheI/EcoRV (λ-leader), EcoRV/HpaI (Vλ- domains), and HpaI/ApaI (λ-chain constant region). The κ-leader (EMBL Z00022) as well as the λ-leader (EMBL L27692) were both equipped with Kozak sequences. The constant regions of the human κ-(EMBL J00241) and λ-chain (EMBL M18645) were assembled by overlap extension-PCR as described above.

Generation of IgG-Expressing CHO-Cells.

CHO-K1 cells were co-transfected with an equimolar mixture of IgG heavy and light chain expression vectors. Double-resistant transfectants were selected with 600 µg/ml G418 and 300 µg/ml Zeocin (Invitrogen) followed by limiting dilution. The supernatant of single clones was assessed for IgG expression by capture-ELISA (see below). Positive clones were expanded in RPMI-1640 medium supplemented with 10% ultra-low IgG-FCS (Life Technologies, Rockville, Md., USA). After adjusting the pH of the supernatant to 8.0 and sterile filtration, the solution was subjected to standard protein A column chromatography (Poros 20 A, PE Biosystems, Foster City, Calif., USA)

All five of the Fabs that showed anti-SCF activity in the TF-1 assay were converted to IgG (A1, A2, A8, D5 and E6). There was insufficient material to test A1 and E6 but the other 3 IgG clones were assayed. At a concentration of 10 ug/ml, A2 and D5 inhibited TF-1 proliferation to the greatest extent and were therefore chosen for affinity optimization.

Example 7

TF-1 Proliferation Assay

The capacity of stem cell factor antibodies to inhibit Stem Cell Factor growth factor activity was measured utilizing a TF1 human hematopoietic cell proliferation assay. In this assay, TF1 cells (American Type Culture Collection, Rockville, Md., USA) were cultured for 4 days in 96 well plates ($1 \times 10^4$/well, 100 µl volume) in RPMI+10% serum with Stem Cell Factor (human from R&D Systems, rat and cyno from Bayer) with or without anti-human Stem Cell Factor murine polyclonal antibody (R&D Systems, catalog #AF-255-NA, Minneapolis, Minn., USA). GM-CSF(R&D Systems) treatment was used as a positive control. Twenty four hours before the final reading, 10 µl Alamar Blue (10% vol, BioSource, Camarillo, Calif., USA) is added to each well. Fluorescence is determined at 530/590 nm using a WAL-LAC Victor 2 fluorometer (Wallac Oy, Turku, Finland).

This assay was used to measure the bioactivity of the Fabs and IgGs, species cross-reactivity of the Fabs and IgGs, and for other preformulation activities.

Stem cell factor was shown to stimulate TF-1 cell proliferation with an $IC_{50}$ of 2 ng/ml while the addition of polyclonal Stem Cell Factor antibodies neutralized this activity with an $IC_{50}$ of 8 µg/ml.

Treatment of TF-1 cells with Fab clones A1, A2, A8, D5 and E6 resulted in inhibition of human, cyno and rat SCF-induced proliferation. All the Fabs inhibited >100% at 200 ug/ml (D5 was only tested up to 120 ug/ml due to limited protein availability). The greater than 100% inhibition could not be accounted for by cytotoxicity (as determined by GM-CSF stimulation of TF-1 proliferation in the presence of 200 ug/ml Fab) or PBS dilution effects. A dose titration of Fabs A1, A2 and E6 indicated very similar dose/response characteristics among the three Fabs. The $IC_{50}$ values for inhibition of cyno SCF were between 20 and 60 ug/ml for all three Fabs tested. The $IC_{50}$ values for inhibition of rat SCF were between 20 and 60 ug/ml for A1 and A2 and between 6.1 and 20 ug/ml for E6. The observation that rat SCF could be inhibited by any of the Fabs was unexpected due to the lack of strong binding between the Fabs and rat SCF as determined by BIAcore assay. The reason for an inhibitory effect in the TF-1 proliferation assays is still unclear but may be due to low affinity binding of the Fabs to rat SCF that is adequate enough to block its interaction with c-kit on the TF1 cells.

Six anti-SCF Fab clones (A2, E6-1, D5, A1, A8, F8) generated using Morphosys technology were screened for bioactivity in the TF-1 proliferation assay. TF-1 cells were stimulated with 10 ng/ml SCF with or without pretreatment with Fab. At 100 ug/ml, 5 out of 6 of the clones (A2, E6-1, D5, A1, A8) inhibited TF-1 proliferation 40% or greater. F8 failed to inhibit any SCF effect at that concentration. A dose titration was done for A1, A8 and F8 (100, 50, 25 and 12.5 ug/ml). There was not enough E6-1 and D5 protein for a full dose titration of those two clones. A1 and A8 both appeared to show some titration of the Fab effect. In a repeat assay, A1 and A8 were titrated (200, 100, 50 and 25 ug/ml) and again showed a dose-dependent effect on SCF-induced proliferation of TF-1 cells. A GM-CSF-stimulated control indicated that the Fabs (A1, A8, F8) were not cytotoxic and did not inhibit the proliferation of the TF-1 cells non-specifically.

More of the Fab protein was expressed for all 5 Fab clones. A side-by-side comparison of the 5 Fab clones (A1, A2, A8, D5, and E6), that inhibited TF-1 proliferation 40% or greater at 100 ug/ml, was performed in a full dose response study (200, 66, 20, 6.6 ug/ml). The five Fab clones were assayed for their ability to inhibit TF-1 proliferation with 10 ng/ml SCF or GM-CSF. All five clones were capable of inhibiting SCF-induced TF-1 proliferation up to 96.6-139.7% at 200 ug/ml. D5 and E6 had the most favorable $IC_{50}$ values (10-12 ug/ml) compared to the other clones, which had $IC_{50}$s of 29-30 ug/ml. None of the clones had an effect on GM-CSF-induced TF-1 proliferation at up to 200 ug/ml suggesting little to no non-specific or cytotoxic effects of the Fab clones on the TF-1 cells. PBS dilution controls indicated no significant effect on proliferation compared to SCF alone. However, there was a trend to lower proliferation with the 1:5 dilution (that used for the 200 ug/ml Fab clone treatment) which may have contributed to the greater than 100% inhibition that was calculated at the highest concentration of 3 of the 5 Fab clones.

In Vitro Testing of Cross Reactivity of the Fabs with Rat and Cyno SCF

In an effort to predict in vivo cross-reactivity of the anti-SCF antibodies, TF-1 cells were stimulated with recombinant SCF from rat and cynomologous monkeys. It was determined that both recombinant cyno and rat SCF were capable of stimulating human TF-1 proliferation in a dose responsive manner. The approximate $IC_{50}$ for human, cyno and rat SCF in the assay were 2, 25 and 17 ng/ml, respectively Example 8

Eosinophil Survival and Activation Assay

The human primary eosinophil survival and activation assays involved isolation of peripheral blood eosinophils and long term culture (i.e. up to 3 days) with or without growth and survival factors such as IL-5 or SCF. These assays were performed to confirm the bioactivity of Fabs and IgGs and evaluate species cross-reactivity in primary cells.

The capacity of stem cell factor antibodies to inhibit Stem Cell Factor-mediated eosinophil survival and activation was determined in cells harvested from human and cynomolgus monkey blood. First, eosinophils are isolated from peripheral blood by negative selection of CD16 using a steel VarioMacs column protocol (Miltenyi Biotec, Auburn, Calif.). This protocol typically returns eosinophils at >95% purity and works equally well for human and cynomolgus monkey blood. Purified eosinophils are then plated at $1 \times 10^5$ cells/well in a 96 well plate with varying concentrations of Stem Cell Factor (R&D Systems) or anti-Stem Cell Factor antibodies.

Supernatants from eosinophils incubated with activation factors such as Stem Cell Factor are assayed for the presence of eosinophil peroxidase, a marker of activation, by the addition of the peroxidase substrate OPD.

The results demonstrated that Stem Cell Factor promotes eosinophil survival in a dose-dependent manner while survival can be inhibited by Stem Cell Factor antibodies, also in a dose-dependent manner.

Activation of eosinophils by Stem Cell Factor can also be inhibited by anti-Stem Cell Factor antibodies. Results demonstrated that anti-Stem Cell Factor antibodies dose dependently decreased the Stem Cell Factor-mediated eosinophil activation.

SCF promotes eosinophil survival in a dose dependent manner and that survival can be inhibited by anti-SCF (10 ug/ml). The anti-apoptotic effect of anti-SCF was also dose dependent.

Example 9

Cockroach Allergen Test Model

The effect of anti-mouse Stem Cell Factor polyclonal antibody (20 mg/kg) in a mouse model of asthma was assessed. The mice were immunized intraperitoneally (i.p.) with cockroach allergen (CRA) in phosphate buffered saline (PBS) on day 0. On day 14 an intranasal challenge of CRA to localize the response to the airway was given. Mice were then rechallenged on day 20 and 22 by intratracheal (i.t.) administration of CRA. The second i.t. challenge is given at a time when there is a considerable amount of inflammation found within and around the airway, including eosinophils. Anti-mouse Stem Cell Factor polyclonal antibody (20 mg/kg) was administered in saline buffer at the time of i.t. CRA challenge. Airway responsiveness to methacholine (AHR) was measured 24 hours after the last CRA challenge with a mouse plethysmograph (Buxco, Trot N.Y.). Airway eosinophil counts were determined 24 h after the last CRA challenge. Anti-mouse Stem Cell Factor polyclonal antibody yielded a 6-fold reduction in the development of AHR versus animals receiving no antibodies. Anti-mouse Stem Cell Factor polyclonal antibody also produced a 2-fold reduction in airway tissue eosinophilia.

The effect of an anti-mouse Stem Cell Factor monoclonal antibody (R&D Systems) was assessed in a CRA mouse model of asthma. Monoclonal antibody (400 ug/kg, 2 mg/kg, or 4 mg/kg) was administered i.t. with CRA on both days of antigen challenge (days 20, 22). Airway responsiveness to methacholine (AHR) and lung cytokine levels were measured as before 6 h after the final CRA challenge. Almost complete inhibition of airway hyperresponsiveness was observed with the lowest dose (400 ug/kg) of antibody tested. Assessment of baseline airway resistance prior to methacholine challenge revealed that the highest dose of monoclonal antibody (4 mg/kg) caused a slight increase in baseline airway resistance. The effect of the monoclonal antibody on various pro-inflammatory chemokines and cytokines was also assessed in this model. A dose-dependent reduction in IL-4, IL-5, tumor necrosis factor (TNF), RANTES and TARC was observed.

Example 10

Optimization of Fab Activity
10.1 Fab Affinity Optimization
Fabs A2 and D5 were optimized for higher affinity binding to human SCF. The CDR3 loops from A2 and D5 were maintained, while the CDR1 and CDR2 loops from both the light and heavy chain were randomized and approximately ten million A2 variants and ten million D5 variants were expressed on the surface of M13 bacteriophage (Morphosys). The CDR1 and CDR2 loops were simultaneously excised from the A2 and D5 kappa light chain variable region with the restriction enzymes PstI and SanDI. Randomized cassettes prepared according to the method in Knappik et al. (2000) containing randomized CDR1 and CDR2 with the intervening Framework 2 region were then inserted to provide A2 and D5 kappa light chain variable regions with randomized CDR1 and CDR2.

The CDR1 region of the A2 and D5 heavy chain variable region VH3 was excised using BspE1 and BssHII and randomized using cassettes prepared according to the method in Knappik et al. (2000). The CDR2 region of the A2 and D5 heavy chain variable region H3 was excised with XhoI and BssHII and randomized using the same type of cassettes.

Three Fab phage libraries were thus created for each of A2 and D5: 1) light chain having randomized CDR1 and CDR2; 2) heavy chain having a randomized CDR1; and 3) heavy chain having a randomized CDR2.

The phagemid expression vector pMORPH18 Fab1 containing the CDR1 and CDR2 libraries was amplified as described in Example 1. The Fab phage libraries were panned for three rounds against human SCF as described in Example 3.

The Fab-encoding inserts of selected HuCAL Fab 1 clones were subcloned into the expression vector pMORPHx7_FS as described in Example 4 to create the Fab expression vector designated pMORPHx9_Fab1_FS. The clones were expressed in *E. coli* and purified using StrepTagII via StrepTactin affinity chromatography (Sigma-Genosys, Woodland, Tex.). The "Strep-tagged" proteins readily bind StrepTactin with high specificity and the protein was eluted from the column upon competition with desthio-biotin. A 1L culture typically yielded 1-3 mg of purified Fab. The expressed Fabs were tested in BiaCORE assays (Uppsala, Sweden). The Fabs with the highest affinity were selected for testing in the TF-1 proliferation assay.

TABLE 5

| Antibody | Additional SCF antibody sequences | |
|---|---|---|
| | DNA sequence of heavy chain CDR1 | Amino acid sequence of heavy chain CDR1 |
| D5-F9 | GGATTTACCTTTAGCTGGAAGGCGATGGCG (SEQ ID NO: 54) | GFTFSWKAMA (SEQ ID NO: 55) |
| | DNA sequence of light chain CDR1 (kappa) | Amino acid sequence of light chain CDR1 |
| A2-A1 | AGAGCGAGCCAGGGCATTAGCAGCTAT CTGGCG (SEQ ID NO: 56) | RASQGISSYLA (SEQ ID NO: 57) |
| A2-G8 | AGAGCGAGCCAGGGCATTCGGGGGTACCT GGGG (SEQ ID NO: 58) | RASQGIRGYLG (SEQ ID NO: 59) |
| A2-E8 | AGAGCGAGCCAGGGCATTTTCAAGTA CCTGGGG (SEQ ID NO: 60) | RASQGIFKYLA (SEQ ID NO: 61) |
| A2-H8 | AGAGCGAGCCAGGGCATTATCGGGT ACCTGGGC (SEQ ID NO: 62) | RASQGIIGYLG (SEQ ID NO: 63) |
| A2-D12 | AGAGCGAGCCAGGGCATTTGGCTGTACC TGTCG (SEQ ID NO: 64) | RASQGIWLYLS (SEQ ID NO: 65) |

TABLE 6

| | DNA sequence of light chain CDR2 (kappa) | Amino acid sequence of light chain CDR2 |
|---|---|---|
| A2-A1 | GCAGCCAGCAGCTTGCAAAGC (SEQ ID NO: 66) | AASSLQS (SEQ ID NO: 67) |
| A-2G8 | TCGGCCAGCAGCTTGCAAAGC (SEQ ID NO: 68) | SASSLQS (SEQ ID NO: 69) |
| A2-E8 | GCGGCCAGCAGCTTGCAAAGC (SEQ ID NO: 70) | AASSLQS (SEQ ID NO: 71) |
| A2-H8 | CGCGCCAGCAGCTTGCAAAGC (SEQ ID NO: 72) | RASSLQS (SEQ ID NO: 73) |
| A2-D12 | GCCGCCAGCAGCTTGCAAAGC (SEQ ID NO: 74) | AASSLQS (SEQ ID NO: 75) |

Conversion to IgG

For transient expression, immunoglobulin expression vectors were constructed in accordance with the method of Example 6. The scFv portion of the Fab heavy chain was inserted into the expression vector pcDNA3.1+ with IgG1 heavy chain constant regions. The scFv portion of the Fab light chain was inserted into the vector pcDNA3.1/Zeo+ with kappa light chain constant regions.

For selection expression, an expression vector containing both heavy and light chains was constructed. The scFv portions of the Fab heavy and light chains were inserted into an expression vector of the type described in U.S. Pat. No. 6,136,599 that contains heavy and light IgG chains. The expression vector also contained the drug resistance gene hph.

The DNA sequence of the light chain variable region of antibody A2-G8:

(SEQ ID NO: 76)
CAGATGACCCAGAGCCCGTCTAGCCTGAGCGCGAGCGTGGGTGATCGTGT

GACCATTACCTGCAGAGCGAGCCAGGGCATTCGGGGGTACCTGGGGTGGT

ACCAGCAGAAACCAGGTAAAGCACCGAAACTATTAATTTATTCGGCCAGC

AGCTTGCAAAGCGGGGTCCCGTCCCGTTTTAGCGGCTCTGGATCCGGCAC

TGATTTTACCCTGACCATTAGCAGCCTGCAACCTGAAGACTTTGCGACCT

ATTATTGCCAGCAGTATTCTGGTATGCCTTATACCTTTGGCCAGGGTACG

AAAGTTGAAATTAAAC

The sequence of the CDR1 region is AGAGCGAGC-CAGGGCATTCGGGGGTA CCTGGGG. The sequence of the CDR2 region is TCGGCCAGCAGCTTGCAAAGC. The sequence of the CDR3 region is CAGCAGTATTCTG-GTATGCCTTAT.

SCF antibody A2-G8 light chain variable and constant region (protein sequence): QMTQSPSSLSASVGDRVTIT-CRASQGIRGYLGWYQQKPGKAP-KLLIYSASSLQSGVPS RFSGSGSGTDFTLTISSLQPED-FATYYCQQYSGMPYTFGQGTKVEIKRTVAAPSVFIFP PSDEQLKSGTASVVCLLNN-FYPREAKVQWKVDNALQSGNSQESVTE-QDSKDSTYSL SSTLTLSKADYEKHKVY-ACEVTHQGLSSPVTKSFNRGEC (SEQ ID NO: 77)

The sequence of the CDR1 region is RASQGIRGYLG. The sequence of the CDR2 region is SASSLQS. The sequence of the CDR3 region is QQYSGMPY.

SCF antibody A2-G8 heavy chain variable region (DNA sequence):

(SEQ ID NO: 78)
TTGGTGGAAAGCGGCGGCGGCCTGGTGCAACCGGGCGGCAGCCTGCGTCT

GAGCTGCGCGGCCTCCGGATTTACCTTTAGCAGCTATGCGATGAGCTGGG

TGCGCCAAGCCCCTGGGAAGGGTCTCGAGTGGGTGAGCGCGATTAGCGGT

AGCGGCGGCAGCACCTATTATGCGGATAGCGTGAAAGGCCGTTTTACCAT

TTCACGTGATAATTCGAAAAACACCCTGTATCTGCAAATGAACAGCCTGC

GTGCGGAAGATACGGCCGTGTATTATTGCGCGCGTCGTGATTTTTTTGCT

CACTTTGATGTTTGGGGCCAAGGCACCCTGGTGACGGTTAGCTCA

The sequence of the CDR1 region is GGATTTACCTT-TAGCAGCTATG CGATGAGC. The sequence of the CDR2 region is GCGATTAGCGGTAGCGGCGGC AGCAC-CTATTATGCGGATAGCGTGAAAGGC. The sequence of the CDR3 region is CGTGATTTTTTTGCTCACTTTGAT-GTT.

SCF antibody A2-G8 heavy chain variable and constant region (protein sequence):

(SEQ ID NO: 79)
LVESGGGLVQPGGSLRLSCAASGFTFSSYAMSWVRQAPGKGLEWVSAISG

SGGSTYYADSVKGRFTISRDNSKNTLYLQMNSLRAEDTAVYYCARRDFFA

HFDVWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK

The sequence of the CDR1 region is GFTFSSYAMS. The sequence of the CDR2 region is AISGSGGSTYYADSVKG. The sequence of the CDR3 region is RDFFAHFDV.

SCF antibody A2-G8 heavy chain constant region (DNA sequence):

(SEQ ID NO: 80)
GCCTCCACCAAGGGTCCATCGGTCTTCCCCCTGGCACCCTCCTCCAAGAG

CACCTCTGGGGGCACAGCGGCCCTGGGCTGCCTGGTCAAGGACTACTTCC

CCGAACCGGTGACGGTGTCGTGGAACTCAGGCGCCCTGACCAGCGGCGTG

CACACCTTCCCGGCTGTCCTACAGTCCTCAGGACTCTACTCCCTCAGCAG

CGTGGTGACCGTGCCCTCCAGCAGCTTGGGCACCCAGACCTACATCTGCA

ACGTGAATCACAAGCCCAGCAACACCAAGGTGGACAAGAAAGTTGAGCCC

AAATCTTGTGACAAAACTCACACATGCCCACCGTGCCCAGCACCTGAACT

CCTGGGGGGACCGTCAGTCTTCCTCTTCCCCCCAAAACCCAAGGACACCC

TCATGATCTCCCGGACCCCTGAGGTCACATGCGTGGTGGTGGACGTGAGC

CACGAAGACCCTGAGGTCAAGTTCAACTGGTACGTGGACGGCGTGGAGGT

GCATAATGCCAAGACAAAGCCGCGGGAGGAGCAGTACAACAGCACGTACC

GGGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAA

AACCATCTCCAAAGCCAAAGGGCAGCCCCGAGAACCACAGGTGTACACCC

TGCCCCCATCCCGGGATGAGCTGACCAAGAACCAGGTCAGCCTGACCTGC

CTGGTCAAAGGCTTCTATCCCAGCGACATCGCCGTGGAGTGGGAGAGCAA

TGGGCAGCCGGAGAACAACTACAAGACCACGCCTCCCGTGCTGGACTCCG

ACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAA

CCACTACACGCAGAAGAGCCTCTCCCTGTCTCCGGGTAAATGA

SCF antibody A2-G8 heavy chain constant region (protein sequence):

ASTKGPSVFPLAPSSKSTSGGTAALGCLVKDYFPEPVTVSWNSGALTSGVHTFPAVL (SEQ ID NO: 81)

QSSGLYSLSSVVTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGK

SCF antibody A2-G8 light chain constant region (DNA sequence) is SEQ ID NO: 82.

SCF antibody A2-G8 light chain constant region (protein sequence) is SEQ ID NO: 83.

IgG Expression

Expression of IgG from HKB11 Cells:

For transient expression HKB11 cells (as described in U.S. Pat. No. 6,136,599) were co-transfected with an equimolar mixture of IgG heavy and light chain expression vectors. The antibody was expressed without selection.

For expression with selection, IgG-heavy and light chain were cloned in a single expression vector also possessing a drug resistant gene (e.g. hph). Three days post transfection of HKB11 cells (200×10⁶ cells) with the expression vector DNA (200 μg), cells were selected with Hygromycin B (50 μg/ml). By feeding the cells twice a week with fresh media, HygB-resistant cells were obtained ~3 weeks post transfection. When stable levels of IgG expression were obtained (5-6 weeks post transfection), cells were scaled up (7 weeks post transfection) and large volume of cells (10 liters) were utilized for production of IgG on a weekly-basis using a Wave Bioreactor to produce smaller amounts of IgG until the required amount of IgG (~100 mg) was obtained. To obtain larger (gram) quantities of IgG, the scaled-up culture had to be inoculated in a fermentor to produce larger volumes of material which took~4 weeks. An additional three weeks were required for affinity purification.

10.2 In Vitro Screening Cascade for Anti-SCF Fabs and IgGs

The first screen was a cell-free binding assay using the BIAcore system to identify Fabs that bound purified SCF. Antibodies showing such activity proceeded to cell-based assays. The second screen was a TF-1 human hematopoietic cell line proliferation assay. SCF stimulates TF-1 cells to proliferate with an $IC_{50}$ of approximately 1 ng/ml. Antibodies that were capable of inhibiting SCF-induced TF-1 proliferation with an $IC_{50}$ of 100 ug/ml or less were tested on primary eosinophils and mast cells in vitro. In vitro survival of eosinophils harvested from either human or Cynomologus monkey peripheral blood can be prolonged by treatment with SCF. Antibodies capable of inhibiting this prolonged survival with an $IC_{50}$ of 100 ug/ml or better proceeded to in vivo screening.

BIAcore Assay

Soluble human, cynomologous (also referred to as "cyno"), and rat SCF were immobilized on a BIAcore sensor chip through amine coupling. Binding to all three forms of SCF was measured for Fabs that were shown to bind to SCF to a level that was at least two-fold over background in a direct ELISA assay. Those antibodies that showed binding to human SCF were scaled up, purified, and decontaminated of endotoxins. These antibodies were further studied in cell-based assays described below.

Biacore Screening Results

Fabs were expressed at small scale and tested for binding using the BIAcore. Six anti-SCF Fabs with binding to human SCF were expressed and tested in the TF-1 proliferation assay. The lead candidates from this assay were Fabs A2 and D5. The affinity of Fabs A2 and D5 were further optimized for higher affinity binding methods through randomization of the CDR1 and CDR2 loops of the heavy and light chains of the Fabs. Fabs derived from this optimization process were screened using BIAcore for binding to SCF. The optimization of the A2 Fabs were most successful, and of these Fabs A2-G8 and Fabs A2-EI were identified as the highest affinity anti-SCF antibodies. These results correlated well with the cell assays described below.

Seven optimized Fabs (A2-A1, A2-D12, A2-E2, A2-E8, A2-G8, A2-H8, D5-F9) were tested in the TF-1 proliferation assay disclosed in Example 7. Clones A2-E8 and A2-G8 had the best inhibitory activity of all the clones and were chosen for conversion into IgG.

TABLE 7

| Antibody | Affinity Estimation | TF-1 Fab assay $IC_{50}$ ug/mL | TF-1 IgG assay $IC_{50}$ ug/mL | Eosinophil IgG assay $IC_{50}$ ug/mL |
|---|---|---|---|---|
| D5-F9 | N.D. | N.D. | N.D. | N.D. |
| A2-A1 | $5.70 \times 10^{-8}$ | 25 | N.D | N.D. |
| A2-G8 | $9.00 \times 10^{-9}$ | 5 | 1 | 1.5 |
| A2-E8 | $1.70 \times 10^{-8}$ | 8 | 6 | 1.1 |
| A2-H8 | $4.40 \times 10^{-8}$ | 25 | N.D | N.D. |
| A2-D12 | $1.80 \times 10^{-8}$ | N.D | N.D | N.D. |

Optimized IgG clones A2-E8 and A2-G8 inhibited TF-1 proliferation equally well with an $IC_{50}$ of 1-6 ug/ml. Likewise, SCF-stimulated human and cyno eosinophil survival was equally affected by pre-treatment with either IgG clone ($IC_{50}$=1.1-8 ug/ml). A summary of the results is shown in Table 8.

TABLE 8

COMPARISON OF $IC_{50}$ CONCENTRATIONS FOR ANTI-SCF CLONES A2-E8 AND A2-G8 IGGS IN 3 CELL-BASED SCREENING ASSAYS.

| | IC50 (ug/ml) | |
|---|---|---|
| | A2-E8 | A2-G8 |
| TF-1 | 6 | 1 |
| Human Eos | 1.1 | 1.5 |
| Cyno Eos | 8 | 3 |

To address concerns about the stability of the anti-SCF antibody following nebulization, a comparison of pre-nebulized material to nebulized material was done in the TF-1 proliferation assay. There was no difference between stock A2-G8 IgG and those samples that were nebulized in SCF blocking ability over a range of doses.

What is claimed is:

1. A purified human antibody which binds to stem cell factor protein, said antibody comprising
   a light chain variable region having the human Vκ1 consensus framework amino acid sequence, wherein light chain CDR 1 has the amino acid sequence of SEQ ID NO:59, light chain CDR 2 has the amino acid sequence of SEQ ID NO:69, and light chain CDR 3 has the amino acid sequence of SEQ ID NO:20; and
   a heavy chain variable region having the human VH3 consensus framework amino acid sequence, wherein heavy chain CDR 1 has the amino acid sequence of residues 23-32 of SEQ ID NO:79, heavy chain CDR 2 has the amino acid sequence of residues 47-63 SEQ ID NO:79, and heavy chain CDR 3 has the amino acid sequence of SEQ ID NO:14,
said antibody being optionally bound to a cytotoxic molecule or detectable label.

2. The antibody of claim 1 wherein said antibody comprises heavy chain variable and constant regions having the amino acid sequence of SEQ ID NO: 77, and light chain variable and constant regions having the amino acid sequence of SEQ ID NO: 79.

3. The antibody of claim 1 wherein said antibody is a full-length antibody.

4. The antibody of claim 1 wherein said antibody is an IgG.

5. The antibody of claim 1 wherein said antibody is an antibody fragment.

6. A preparation comprising the antibody of claim 1.

7. A pharmaceutical composition comprising the antibody of claim 1 and a pharmaceutically acceptable carrier.

* * * * *

SEQUENCE LISTING

<160> NUMBER OF SEQ ID NOS: 85

<210> SEQ ID NO 1
<211> LENGTH: 36
<212> TYPE: DNA
<213> ORGANISM: Artificial
<220> FEATURE:
<223> OTHER INFORMATION: Synthetic sequence

<400> SEQUENCE: 1
ggtattaatt ctcgtcgtca gcgtcagttt gattat                          36

<210> SEQ ID NO 2
<211> LENGTH: 27
<212> TYPE: DNA
<213> ORGANISM: Artificial
<220> FEATURE:
<223> OTHER INFORMATION: synthetic sequence

<400> SEQUENCE: 2
cgtgattttt ttgctcactt tgatgtt                                    27

<210> SEQ ID NO 3
<211> LENGTH: 24
<212> TYPE: DNA
<213> ORGANISM: Artificial
<220> FEATURE:
<223> OTHER INFORMATION: synthetic sequence

<400> SEQUENCE: 3
ggttattttg atgagtttga tgtt                                       24

<210> SEQ ID NO 4
<211> LENGTH: 21
<212> TYPE: DNA
<213> ORGANISM: Artificial
<220> FEATURE:
<223> OTHER INFORMATION: synthetic sequence

<400> SEQUENCE: 4
tattcttatt attttgatgt t                                          21

<210> SEQ ID NO 5
<211> LENGTH: 57
<212> TYPE: DNA
<213> ORGANISM: Artificial
<220> FEATURE:
<223> OTHER INFORMATION: synthetic sequence

<400> SEQUENCE: 5
aattattctt ctccttttgg ttatatgttt cttatttctt attatgcttt tgataat    57

<210> SEQ ID NO 6
<211> LENGTH: 36
<212> TYPE: DNA
<213> ORGANISM: Artificial
<220> FEATURE:
<223> OTHER INFORMATION: synthetic sequence

<400> SEQUENCE: 6
tatggttatt ttctttataa tggtgatttt gataat                          36

<210> SEQ ID NO 7
<211> LENGTH: 24

-continued

```
<212> TYPE: DNA
<213> ORGANISM: Artificial
<220> FEATURE:
<223> OTHER INFORMATION: synthetic sequence

<400> SEQUENCE: 7
cagcagtatg gttctatttc tact                                          24

<210> SEQ ID NO 8
<211> LENGTH: 24
<212> TYPE: DNA
<213> ORGANISM: Artificial
<220> FEATURE:
<223> OTHER INFORMATION: synthetic sequence

<400> SEQUENCE: 8
cagcagtatt ctggtatgcc ttat                                          24

<210> SEQ ID NO 9
<211> LENGTH: 24
<212> TYPE: DNA
<213> ORGANISM: Artificial
<220> FEATURE:
<223> OTHER INFORMATION: synthetic sequence

<400> SEQUENCE: 9
cagcagtttg atatgtttcc tgat                                          24

<210> SEQ ID NO 10
<211> LENGTH: 24
<212> TYPE: DNA
<213> ORGANISM: Artificial
<220> FEATURE:
<223> OTHER INFORMATION: synthetic sequence

<400> SEQUENCE: 10
cagcagatta attctcgtcc tcct                                          24

<210> SEQ ID NO 11
<211> LENGTH: 24
<212> TYPE: DNA
<213> ORGANISM: Artificial
<220> FEATURE:
<223> OTHER INFORMATION: synthetic sequence

<400> SEQUENCE: 11
cagagctatg accatcctct tatt                                          24

<210> SEQ ID NO 12
<211> LENGTH: 30
<212> TYPE: DNA
<213> ORGANISM: Artificial
<220> FEATURE:
<223> OTHER INFORMATION: synthetic sequence

<400> SEQUENCE: 12
cagagccgtg accattatgt tgttcgttgg                                    30

<210> SEQ ID NO 13
<211> LENGTH: 12
<212> TYPE: PRT
<213> ORGANISM: Artificial
<220> FEATURE:
<223> OTHER INFORMATION: synthetic sequence

<400> SEQUENCE: 13
```

```
Gly Ile Asn Ser Arg Arg Gln Arg Gln Phe Asp Tyr
1               5                   10
```

<210> SEQ ID NO 14
<211> LENGTH: 9
<212> TYPE: PRT
<213> ORGANISM: Artificial
<220> FEATURE:
<223> OTHER INFORMATION: synthetic sequence

<400> SEQUENCE: 14

```
Arg Asp Phe Phe Ala His Phe Asp Val
1               5
```

<210> SEQ ID NO 15
<211> LENGTH: 8
<212> TYPE: PRT
<213> ORGANISM: Artificial
<220> FEATURE:
<223> OTHER INFORMATION: synthetic sequence

<400> SEQUENCE: 15

```
Gly Tyr Phe Asp Glu Phe Asp Val
1               5
```

<210> SEQ ID NO 16
<211> LENGTH: 7
<212> TYPE: PRT
<213> ORGANISM: Artificial
<220> FEATURE:
<223> OTHER INFORMATION: synthetic sequence

<400> SEQUENCE: 16

```
Tyr Ser Tyr Tyr Phe Asp Val
1               5
```

<210> SEQ ID NO 17
<211> LENGTH: 19
<212> TYPE: PRT
<213> ORGANISM: Artificial
<220> FEATURE:
<223> OTHER INFORMATION: synthetic sequence

<400> SEQUENCE: 17

```
Asn Tyr Ser Ser Pro Phe Gly Tyr Met Phe Leu Ile Ser Tyr Tyr Ala
1               5                   10                  15
Phe Asp Asn
```

<210> SEQ ID NO 18
<211> LENGTH: 12
<212> TYPE: PRT
<213> ORGANISM: Artificial
<220> FEATURE:
<223> OTHER INFORMATION: synthetic sequence

<400> SEQUENCE: 18

```
Tyr Gly Tyr Phe Leu Tyr Asn Gly Asp Phe Asp Asn
1               5                   10
```

<210> SEQ ID NO 19
<211> LENGTH: 8
<212> TYPE: PRT
<213> ORGANISM: Artificial
<220> FEATURE:
<223> OTHER INFORMATION: synthetic sequence

<400> SEQUENCE: 19

```
Gln Gln Tyr Gly Ser Ile Ser Thr
1               5
```

<210> SEQ ID NO 20
<211> LENGTH: 8
<212> TYPE: PRT
<213> ORGANISM: Artificial
<220> FEATURE:
<223> OTHER INFORMATION: synthetic sequence

<400> SEQUENCE: 20

```
Gln Gln Tyr Ser Gly Met Pro Tyr
1               5
```

<210> SEQ ID NO 21
<211> LENGTH: 8
<212> TYPE: PRT
<213> ORGANISM: Artificial
<220> FEATURE:
<223> OTHER INFORMATION: synthetic sequence

<400> SEQUENCE: 21

```
Gln Gln Phe Asp Met Phe Pro Asp
1               5
```

<210> SEQ ID NO 22
<211> LENGTH: 8
<212> TYPE: PRT
<213> ORGANISM: Artificial
<220> FEATURE:
<223> OTHER INFORMATION: synthetic sequence

<400> SEQUENCE: 22

```
Gln Gln Ile Asn Ser Arg Pro Pro
1               5
```

<210> SEQ ID NO 23
<211> LENGTH: 8
<212> TYPE: PRT
<213> ORGANISM: Artificial
<220> FEATURE:
<223> OTHER INFORMATION: synthetic sequence

<400> SEQUENCE: 23

```
Gln Ser Tyr Asp His Pro Leu Ile
1               5
```

<210> SEQ ID NO 24
<211> LENGTH: 10
<212> TYPE: PRT
<213> ORGANISM: Artificial
<220> FEATURE:
<223> OTHER INFORMATION: synthetic sequence

<400> SEQUENCE: 24

```
Gln Ser Arg Asp His Tyr Val Val Arg Trp
1               5                   10
```

<210> SEQ ID NO 25
<211> LENGTH: 165
<212> TYPE: PRT
<213> ORGANISM: Homo sapiens

<400> SEQUENCE: 25

```
Met Glu Gly Ile Cys Arg Asn Arg Val Thr Asn Asn Val Lys Asp Val
1               5                   10                  15
```

-continued

```
Thr Lys Leu Val Ala Asn Leu Pro Lys Asp Tyr Met Ile Thr Leu Lys
             20                  25                  30

Tyr Val Pro Gly Met Asp Val Leu Pro Ser His Cys Trp Ile Ser Glu
         35                  40                  45

Met Val Val Gln Leu Ser Asp Ser Leu Thr Asp Leu Leu Asp Lys Phe
     50                  55                  60

Ser Asn Ile Ser Glu Gly Leu Ser Asn Tyr Ser Ile Ile Asp Lys Leu
 65                  70                  75                  80

Val Asn Ile Val Asp Asp Leu Val Glu Cys Val Lys Glu Asn Ser Ser
                 85                  90                  95

Lys Asp Leu Lys Lys Ser Phe Lys Ser Pro Glu Pro Arg Leu Phe Thr
            100                 105                 110

Pro Glu Glu Phe Phe Arg Ile Phe Asn Arg Ser Ile Asp Ala Phe Lys
        115                 120                 125

Asp Phe Val Val Ala Ser Glu Thr Ser Asp Cys Val Val Ser Ser Thr
130                 135                 140

Leu Ser Pro Glu Lys Asp Ser Arg Val Ser Val Thr Lys Pro Phe Met
145                 150                 155                 160

Leu Pro Pro Val Ala
            165

<210> SEQ ID NO 26
<211> LENGTH: 109
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (85)..(85)
<223> OTHER INFORMATION: Xaa is Threonine or valine
<220> FEATURE:
<221> NAME/KEY: MISC_FEATURE
<222> LOCATION: (89)..(89)
<223> OTHER INFORMATION: Xaa is any amino acid
<220> FEATURE:
<221> NAME/KEY: MISC_FEATURE
<222> LOCATION: (91)..(96)
<223> OTHER INFORMATION: each occurrence of Xaa is any amino acid

<400> SEQUENCE: 26

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Xaa Tyr Tyr Cys Xaa Gln Xaa Xaa Xaa Xaa Xaa Xaa
                 85                  90                  95

Thr Phe Gly Gln Gly Thr Lys Val Glu Ile Lys Arg Thr
            100                 105

<210> SEQ ID NO 27
<211> LENGTH: 114
<212> TYPE: PRT
<213> ORGANISM: Artificial
<220> FEATURE:
```

```
<223> OTHER INFORMATION: synthetic sequence
<220> FEATURE:
<221> NAME/KEY: MISC_FEATURE
<222> LOCATION: (94)..(94)
<223> OTHER INFORMATION: Xaa is any amino acid
<220> FEATURE:
<221> NAME/KEY: MISC_FEATURE
<222> LOCATION: (96)..(101)
<223> OTHER INFORMATION: each occurrence of Xaa is any amino acid

<400> SEQUENCE: 27

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Xaa Gln Xaa
                 85                  90                  95

Xaa Xaa Xaa Xaa Xaa Thr Phe Gly Gln Gly Thr Lys Val Glu Ile Lys
             100                 105                 110
Arg Thr

<210> SEQ ID NO 28
<211> LENGTH: 110
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (86)..(86)
<223> OTHER INFORMATION: Xaa is threonine or valine
<220> FEATURE:
<221> NAME/KEY: MISC_FEATURE
<222> LOCATION: (90)..(90)
<223> OTHER INFORMATION: Xaa is any amino acid
<220> FEATURE:
<221> NAME/KEY: MISC_FEATURE
<222> LOCATION: (92)..(97)
<223> OTHER INFORMATION: each occurrence of Xaa is any amino acid

<400> SEQUENCE: 28

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Val Pro Ala Arg Phe Ser
     50                  55                  60

Gly Ser Gly Ser Gly Thr Asp Phe Thr Leu Thr Ile Ser Ser Leu Glu
 65                  70                  75                  80

Pro Glu Asp Phe Ala Xaa Tyr Tyr Cys Xaa Gln Xaa Xaa Xaa Xaa Xaa
                 85                  90                  95

Xaa Thr Phe Gly Gln Gly Thr Lys Val Glu Ile Lys Arg Thr
             100                 105                 110

<210> SEQ ID NO 29
```

```
<211> LENGTH: 115
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (95)..(95)
<223> OTHER INFORMATION: Xaa is any amino acid
<220> FEATURE:
<221> NAME/KEY: MISC_FEATURE
<222> LOCATION: (97)..(102)
<223> OTHER INFORMATION: each occurrence of Xaa is any amino acid

<400> SEQUENCE: 29

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Xaa Gln
                85                  90                  95

Xaa Xaa Xaa Xaa Xaa Xaa Thr Phe Gly Gln Gly Thr Lys Val Glu Ile
            100                 105                 110

Lys Arg Thr
        115

<210> SEQ ID NO 30
<211> LENGTH: 111
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (92)..(92)
<223> OTHER INFORMATION: Xaa is any amino acid
<220> FEATURE:
<221> NAME/KEY: MISC_FEATURE
<222> LOCATION: (94)..(99)
<223> OTHER INFORMATION: each occurrence of Xaa is any amino acid

<400> SEQUENCE: 30

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Xaa Asp Xaa Xaa Xaa
                85                  90                  95

Xaa Xaa Xaa Val Phe Gly Gly Gly Thr Lys Leu Thr Val Leu Gly
            100                 105                 110
```

<210> SEQ ID NO 31
<211> LENGTH: 112
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (93)..(93)
<223> OTHER INFORMATION: Xaa is any amino acid
<220> FEATURE:
<221> NAME/KEY: MISC_FEATURE
<222> LOCATION: (95)..(100)
<223> OTHER INFORMATION: each occurrence of Xaa is any amino acid

<400> SEQUENCE: 31

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Xaa Asp Xaa Xaa
                85                  90                  95

Xaa Xaa Xaa Xaa Val Phe Gly Gly Gly Thr Lys Leu Thr Val Leu Gly
            100                 105                 110

<210> SEQ ID NO 32
<211> LENGTH: 109
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (90)..(90)
<223> OTHER INFORMATION: Xaa is any amino acid
<220> FEATURE:
<221> NAME/KEY: MISC_FEATURE
<222> LOCATION: (92)..(97)
<223> OTHER INFORMATION: each occurrence of Xaa is any amino acid

<400> SEQUENCE: 32

Asp Ile Glu Leu Thr Gln Pro Pro Ser Val Ser Val Ala Pro Gly Gln
1               5                   10                  15

Thr Ala Arg Ile Ser Cys Ser Gly Asp Ala Leu Gly Asp Lys Tyr Ala
                20                  25                  30

Ser Trp Tyr Gln Gln Lys Pro Gly Gln Ala Pro Val Leu Val Ile Tyr
            35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Xaa Asp Xaa Xaa Xaa Xaa Xaa
                85                  90                  95

Xaa Val Phe Gly Gly Gly Thr Lys Leu Thr Val Leu Gly
            100                 105

```
<210> SEQ ID NO 33
<211> LENGTH: 127
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (99)..(114)
<223> OTHER INFORMATION: each occurrence of Xaa is any amino acid
<220> FEATURE:
<221> NAME/KEY: MISC_FEATURE
<222> LOCATION: (116)..(116)
<223> OTHER INFORMATION: Xaa is any amino acid

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Xaa Xaa Xaa Xaa Xaa Xaa Xaa Xaa Xaa Xaa Xaa Xaa Xaa Xaa
            100                 105                 110

Xaa Xaa Asp Xaa Trp Gly Gln Gly Thr Leu Val Thr Val Ser Ser
        115                 120                 125

<210> SEQ ID NO 34
<211> LENGTH: 127
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (99)..(114)
<223> OTHER INFORMATION: each occurrence of Xaa is any amino acid
<220> FEATURE:
<221> NAME/KEY: MISC_FEATURE
<222> LOCATION: (116)..(116)
<223> OTHER INFORMATION: Xaa is any amino acid

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Xaa Xaa Xaa Xaa Xaa Xaa Xaa Xaa Xaa Xaa Xaa Xaa Xaa Xaa
            100                 105                 110
```

```
Xaa Xaa Asp Xaa Trp Gly Gln Gly Thr Leu Val Thr Val Ser Ser
        115                 120                 125

<210> SEQ ID NO 35
<211> LENGTH: 128
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (100)..(115)
<223> OTHER INFORMATION: each occurrence of Xaa is any amino acid
<220> FEATURE:
<221> NAME/KEY: MISC_FEATURE
<222> LOCATION: (117)..(117)
<223> OTHER INFORMATION: Xaa is any amino acid

<400> SEQUENCE: 35

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Xaa Xaa Xaa Xaa Xaa Xaa Xaa Xaa Xaa Xaa Xaa Xaa Xaa
            100                 105                 110

Xaa Xaa Xaa Asp Xaa Trp Gly Gln Gly Thr Leu Val Thr Val Ser Ser
        115                 120                 125

<210> SEQ ID NO 36
<211> LENGTH: 127
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (99)..(114)
<223> OTHER INFORMATION: each occurrence of Xaa is any amino acid
<220> FEATURE:
<221> NAME/KEY: MISC_FEATURE
<222> LOCATION: (116)..(116)
<223> OTHER INFORMATION: Xaa is any amino acid

<400> SEQUENCE: 36

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Xaa Xaa Xaa Xaa Xaa Xaa Xaa Xaa Xaa Xaa Xaa Xaa Xaa Xaa
            100                 105                 110

Xaa Xaa Asp Xaa Trp Gly Gln Gly Thr Leu Val Thr Val Ser Ser
        115                 120                 125

<210> SEQ ID NO 37
<211> LENGTH: 126
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (98)..(113)
<223> OTHER INFORMATION: each occurrence of Xaa is any amino acid
<220> FEATURE:
<221> NAME/KEY: MISC_FEATURE
<222> LOCATION: (115)..(115)
<223> OTHER INFORMATION: Xaa is any amino acid

<400> SEQUENCE: 37

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Xaa Xaa Xaa Xaa Xaa Xaa Xaa Xaa Xaa Xaa Xaa Xaa Xaa Xaa Xaa
            100                 105                 110

Xaa Asp Xaa Trp Gly Gln Gly Thr Leu Val Thr Val Ser Ser
        115                 120                 125

<210> SEQ ID NO 38
<211> LENGTH: 127
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (99)..(114)
<223> OTHER INFORMATION: each occurrence of Xaa is any amino acid
<220> FEATURE:
<221> NAME/KEY: MISC_FEATURE
<222> LOCATION: (116)..(116)
<223> OTHER INFORMATION: Xaa is any amino acid

<400> SEQUENCE: 38

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
```

-continued

```
                 50                  55                  60
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Xaa Xaa Xaa Xaa Xaa Xaa Xaa Xaa Xaa Xaa Xaa Xaa Xaa Xaa
                100                 105                 110

Xaa Xaa Asp Xaa Trp Gly Gln Gly Thr Leu Val Thr Val Ser Ser
                115                 120                 125

<210> SEQ ID NO 39
<211> LENGTH: 130
<212> TYPE: PRT
<213> ORGANISM: Artificial
<220> FEATURE:
<223> OTHER INFORMATION: synthetic sequence
<220> FEATURE:
<221> NAME/KEY: MISC_FEATURE
<222> LOCATION: (102)..(117)
<223> OTHER INFORMATION: each occurrence of Xaa is any amino acid
<220> FEATURE:
<221> NAME/KEY: MISC_FEATURE
<222> LOCATION: (119)..(119)
<223> OTHER INFORMATION: Xaa is any amino acid

<400> SEQUENCE: 39

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
                 20                  25                  30

Ser Ala Ala Trp Asn Trp Ile Arg Gln Ser Pro Gly Arg Gly Leu Glu
                 35                  40                  45

Trp Leu Gly Arg Thr Tyr Tyr Arg Ser Lys Trp Tyr Asn Asp Tyr Ala
         50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Xaa Xaa Xaa Xaa Xaa Xaa Xaa Xaa Xaa Xaa Xaa
                100                 105                 110

Xaa Xaa Xaa Xaa Xaa Asp Xaa Trp Gly Gln Gly Thr Leu Val Thr Val
            115                 120                 125

Ser Ser
    130

<210> SEQ ID NO 40
<211> LENGTH: 327
<212> TYPE: DNA
<213> ORGANISM: Artificial
<220> FEATURE:
<223> OTHER INFORMATION: synthetic sequence
<220> FEATURE:
<221> NAME/KEY: misc_feature
<222> LOCATION: (253)..(253)
<223> OTHER INFORMATION: N is A or G
<220> FEATURE:
<221> NAME/KEY: misc_feature
<222> LOCATION: (254)..(254)
<223> OTHER INFORMATION: N is C or T
<220> FEATURE:
<221> NAME/KEY: misc_feature
<222> LOCATION: (265)..(267)
<223> OTHER INFORMATION: bases 265-267 encode any amino acid
<220> FEATURE:
```

```
<221> NAME/KEY: misc_feature
<222> LOCATION: (271)..(288)
<223> OTHER INFORMATION: bases 271- 288 encode a randomized sequence of
      any 6 amino acids

<400> SEQUENCE: 40
gatatccaga tgacccagag cccgtctagc ctgagcgcga gcgtgggtga tcgtgtgacc    60
attacctgca gagcgagcca gggcattagc agctatctgg cgtggtacca gcagaaacca   120
ggtaaagcac cgaaactatt aatttatgca gccagcagct tgcaaagcgg ggtcccgtcc   180
cgttttagcg gctctggatc cggcactgat tttaccctga ccattagcag cctgcaacct   240
gaagactttg cgnnttatta ttgcnnncag nnnnnnnnnn nnnnnnnnac ctttggccag   300
ggtacgaaag ttgaaattaa acgtacg                                       327

<210> SEQ ID NO 41
<211> LENGTH: 342
<212> TYPE: DNA
<213> ORGANISM: Artificial
<220> FEATURE:
<223> OTHER INFORMATION: synthetic sequence
<220> FEATURE:
<221> NAME/KEY: misc_feature
<222> LOCATION: (280)..(282)
<223> OTHER INFORMATION: bases 280-282 encode any amino acid
<220> FEATURE:
<221> NAME/KEY: misc_feature
<222> LOCATION: (286)..(303)
<223> OTHER INFORMATION: bases 286 - 303 encode a randomized sequence of
      any 6 amino acids

<400> SEQUENCE: 41
gatatcgtga tgacccagag cccactgagc ctgccagtga ctccgggcga gcctgcgagc    60
attagctgca gaagcagcca aagcctgctg catagcaacg gctataacta tctggattgg   120
taccttcaaa aaccaggtca aagcccgcag ctattaattt atctgggcag caaccgtgcc   180
agtggggtcc cggatcgttt tagcggctct ggatccggca ccgattttac cctgaaaatt   240
agccgtgtgg aagctgaaga cgtgggcgtg tattattgcn nncagnnnnn nnnnnnnnnn   300
nnnacctttg gccagggtac gaaagttgaa attaaacgta cg                      342

<210> SEQ ID NO 42
<211> LENGTH: 330
<212> TYPE: DNA
<213> ORGANISM: Artificial
<220> FEATURE:
<223> OTHER INFORMATION: synthetic sequence
<220> FEATURE:
<221> NAME/KEY: misc_feature
<222> LOCATION: (256)..(256)
<223> OTHER INFORMATION: N is A or G
<220> FEATURE:
<221> NAME/KEY: misc_feature
<222> LOCATION: (257)..(257)
<223> OTHER INFORMATION: N is C or T
<220> FEATURE:
<221> NAME/KEY: misc_feature
<222> LOCATION: (268)..(270)
<223> OTHER INFORMATION: bases 268 - 270 encode any amino acid
<220> FEATURE:
<221> NAME/KEY: misc_feature
<222> LOCATION: (274)..(291)
<223> OTHER INFORMATION: bases 274 - 291 encode a randomized sequence of
      any 6 amino acids

<400> SEQUENCE: 42
gatatcgtgc tgacccagag cccggcgacc ctgagcctgt ctccgggcga acgtgcgacc    60
```

-continued

```
ctgagctgca gagcgagcca gagcgtgagc agcagctatc tggcgtggta ccagcagaaa      120
ccaggtcaag caccgcgtct attaatttat ggcgcgagca gccgtgcaac tggggtcccg      180
gcgcgtttta gcggctctgg atccggcacg gattttaccc tgaccattag cagcctggaa      240
cctgaagact ttgcgnntta ttattgcnnn cagnnnnnnn nnnnnnnnnn nacctttggc      300
cagggtacga agttgaaat taaacgtacg                                        330
```

<210> SEQ ID NO 43
<211> LENGTH: 345
<212> TYPE: DNA
<213> ORGANISM: Artificial
<220> FEATURE:
<223> OTHER INFORMATION: synthetic sequence
<220> FEATURE:
<221> NAME/KEY: misc_feature
<222> LOCATION: (283)..(285)
<223> OTHER INFORMATION: bases 283 - 285 encode any amino acid
<220> FEATURE:
<221> NAME/KEY: misc_feature
<222> LOCATION: (289)..(306)
<223> OTHER INFORMATION: bases 289 - 306 encode a randomized sequence of
    any 6 amino acids

<400> SEQUENCE: 43

```
gatatcgtga tgacccagag cccggatagc ctggcggtga gcctgggcga acgtgcgacc      60
attaactgca gaagcagcca gagcgtgctg tatagcagca caacaaaaa ctatctggcg      120 tggtaccagc agaaaccagg tcagccgccg aaactattaa tttattgggc atccacccgt      180
gaaagcgggg tcccggatcg ttttagcggc tctggatccg gcactgattt taccctgacc      240
atttcgtccc tgcaagctga agacgtggcg gtgtattatt gcnnncagnn nnnnnnnnn      300 nnnnnnacct tggccaggg tacgaaagtt gaaattaaac gtacg                       345
```

<210> SEQ ID NO 44
<211> LENGTH: 336
<212> TYPE: DNA
<213> ORGANISM: Artificial
<220> FEATURE:
<223> OTHER INFORMATION: synthetic sequence
<220> FEATURE:
<221> NAME/KEY: misc_feature
<222> LOCATION: (274)..(276)
<223> OTHER INFORMATION: bases 274 - 276 encode any amino acid
<220> FEATURE:
<221> NAME/KEY: misc_feature
<222> LOCATION: (280)..(297)
<223> OTHER INFORMATION: bases 280 - 297 encode a randomized sequence of
    any 6 amino acids

<400> SEQUENCE: 44

```
gatatcgtgc tgacccagcc gccttcagtg agtggcgcac caggtcagcg tgtgaccatc      60
tcgtgtagcg gcagcagcag caacattggc agcaactatg tgagctggta ccagcagttg      120
cccgggacgg cgccgaaact gctgatttat gataacaacc agcgtccctc aggcgtgccg      180
gatcgtttta gcggatccaa agcggcacc agcgcgagcc ttgcgattac gggcctgcaa      240
agcgaagacg aagcggatta ttattgccag tctnnngatn nnnnnnnnnn nnnnnngtg      300 tttggcggcg gcacgaagtt aaccgttctt ggccag                               336
```

<210> SEQ ID NO 45
<211> LENGTH: 339
<212> TYPE: DNA
<213> ORGANISM: Artificial
<220> FEATURE:
<223> OTHER INFORMATION: synthetic sequence

```
<220> FEATURE:
<221> NAME/KEY: misc_feature
<222> LOCATION: (277)..(279)
<223> OTHER INFORMATION: bases 277 - 279 encode any amino acid
<220> FEATURE:
<221> NAME/KEY: misc_feature
<222> LOCATION: (283)..(300)
<223> OTHER INFORMATION: bases 283 - 300 encode a randomized sequence of
      any 6 amino acids

<400> SEQUENCE: 45
gatatcgcac tgacccagcc agcttcagtg agcggctcac caggtcagag cattaccatc      60
tcgtgtacgg gtactagcag cgatgtgggc ggctataact atgtgagctg gtaccagcag     120
catcccggga aggcgccgaa actgatgatt tatgatgtga gcaaccgtcc ctcaggcgtg     180
agcaaccgtt ttagcggatc caaaagcggc aacaccgcga gcctgaccat tagcggcctg     240
caagcggaag acgaagcgga ttattattgc cagtctnnng atnnnnnnnn nnnnnnnnnn     300
gtgtttggcg gcggcacgaa gttaaccgtt cttggccag                            339

<210> SEQ ID NO 46
<211> LENGTH: 330
<212> TYPE: DNA
<213> ORGANISM: Artificial
<220> FEATURE:
<223> OTHER INFORMATION: synthetic sequence
<220> FEATURE:
<221> NAME/KEY: misc_feature
<222> LOCATION: (268)..(270)
<223> OTHER INFORMATION: bases 268 - 270 encode any amino acid
<220> FEATURE:
<221> NAME/KEY: misc_feature
<222> LOCATION: (274)..(291)
<223> OTHER INFORMATION: bases 274 - 291 encode a randomized sequence of
      any 6 amino acids

<400> SEQUENCE: 46
gatatcgaac tgacccagcc gccttcagtg agcgttgcac caggtcagac cgcgcgtatc      60
tcgtgtagcg gcgatgcgct gggcgataaa tacgcgagct ggtaccagca gaaacccggg     120
caggcgccaa ttctggtgat ttatgatgat tctgaccgtc cctcaggcat cccggaacgc     180
tttagcggat ccaacagcgg caacaccgcg accctgacca ttagcggcac tcaggcggaa     240
gacgaagcgg attattattg ccagtctnnn gatnnnnnnn nnnnnnnnnn ngtgtttggc     300
ggcggcacga agttaaccgt tcttggccag                                      330

<210> SEQ ID NO 47
<211> LENGTH: 383
<212> TYPE: DNA
<213> ORGANISM: Artificial
<220> FEATURE:
<223> OTHER INFORMATION: synthetic sequence
<220> FEATURE:
<221> NAME/KEY: misc_feature
<222> LOCATION: (295)..(342)
<223> OTHER INFORMATION: bases 295 - 342 encode a randomized sequence of
      any 16 amino acids
<220> FEATURE:
<221> NAME/KEY: misc_feature
<222> LOCATION: (346)..(348)
<223> OTHER INFORMATION: bases 346 - 348 encode any amino acid

<400> SEQUENCE: 47
caggtgcaat tggttcagtc tggcgcggaa gtgaaaaaac cgggcagcag cgtgaaagtg      60
agctgcaaag cctccggagg cacttttagc agctatgcga ttagctgggt cgcgcaagcc     120
cctgggcagg gtctcgagtg gatgggcggc attattccga ttttttggca cggcgaactac    180
```

-continued

```
gcgcagaagt tcagggccg ggtgaccatt accgcggatg aaagcaccag caccgcgtat      240
atggaactga gcagcctgcg tagcgaagat acggccgtgt attattgcgc gcgtnnnnnn    300
nnnnnnnnnn nnnnnnnnnn nnnnnnnnnn nnnnnnnnnn nngatnnntg gggccaaggc    360
accctggtga cggttagctc agc                                            383
```

<210> SEQ ID NO 48
<211> LENGTH: 383
<212> TYPE: DNA
<213> ORGANISM: Artificial
<220> FEATURE:
<223> OTHER INFORMATION: synthetic sequence
<220> FEATURE:
<221> NAME/KEY: misc_feature
<222> LOCATION: (295)..(342)
<223> OTHER INFORMATION: bases 295 - 342 encode a randomized sequence of
      any sixteen amino acids
<220> FEATURE:
<221> NAME/KEY: misc_feature
<222> LOCATION: (346)..(348)
<223> OTHER INFORMATION: bases 346 - 348 encode any amino acid

<400> SEQUENCE: 48

```
caggtgcaat tggttcagag cggcgcggaa gtgaaaaaac cgggcgcgag cgtgaaagtg      60
agctgcaaag cctccggata tacctttacc agctattata tgcactgggt ccgccaagcc    120
cctgggcagg gtctcgagtg gatgggctgg attaacccga atagcggcgg cacgaactac    180
gcgcagaagt tcagggccg ggtgaccatg accgtgata ccagcattag caccgcgtat      240
atggaactga gcagcctgcg tagcgaagat acggccgtgt attattgcgc gcgtnnnnnn    300
nnnnnnnnnn nnnnnnnnnn nnnnnnnnnn nnnnnnnnnn nngatnnntg gggccaaggc    360
accctggtga cggttagctc agc                                            383
```

<210> SEQ ID NO 49
<211> LENGTH: 386
<212> TYPE: DNA
<213> ORGANISM: Artificial
<220> FEATURE:
<223> OTHER INFORMATION: synthetic sequence
<220> FEATURE:
<221> NAME/KEY: misc_feature
<222> LOCATION: (298)..(345)
<223> OTHER INFORMATION: bases 298 - 345 encode a randomized sequence of
      any 16 amino acids
<220> FEATURE:
<221> NAME/KEY: misc_feature
<222> LOCATION: (349)..(351)
<223> OTHER INFORMATION: bases 349-351 encode any amino acid

<400> SEQUENCE: 49

```
caggtgcaat tgaaagaaag cggcccggcc ctggtgaaac cgacccaaac cctgaccctg      60
acctgtacct tttccggatt tagcctgtcc acgtctggcg ttggcgtggg ctggattcgc    120
cagccgcctg ggaaagccct cgagtggctg gctctgattg attgggatga tgataagtat    180
tatagcacca gcctgaaaac gcgtctgacc attagcaaag atacttcgaa aaatcaggtg    240
gtgctgacta tgaccaacat ggacccggtg gatacggcca cctattattg cgcgcgtnnn    300
nnnnnnnnnn nnnnnnnnnn nnnnnnnnnn nnnnnnnnnn nnnnngatnn ntggggccaa    360
ggcaccctgg tgacggttag ctcagc                                          386
```

<210> SEQ ID NO 50
<211> LENGTH: 383
<212> TYPE: DNA

```
<213> ORGANISM: Artificial
<220> FEATURE:
<223> OTHER INFORMATION: synthetic sequence
<220> FEATURE:
<221> NAME/KEY: misc_feature
<222> LOCATION: (295)..(342)
<223> OTHER INFORMATION: bases 295 - 342 encode a randomized sequence of
      any 16 amino acids
<220> FEATURE:
<221> NAME/KEY: misc_feature
<222> LOCATION: (346)..(348)
<223> OTHER INFORMATION: bases 346 - 348 encode any amino acid

<400> SEQUENCE: 50
caggtgcaat tggtggaaag cggcggcggc ctggtgcaac cgggcggcag cctgcgtctg      60
agctgcgcgg cctccggatt tacctttagc agctatgcga tgagctgggt gcgccaagcc     120
cctgggaagg gtctcgagtg ggtgagcgcg attagcggta gcggcggcag cacctattat     180
gcggatagcg tgaaaggccg ttttaccatt tcacgtgata attcgaaaaa caccctgtat     240
ctgcaaatga acagcctgcg tgcggaagat acggccgtgt attattgcgc gcgtnnnnnn     300
nnnnnnnnnn nnnnnnnnnn nnnnnnnnnn nnnnnnnnnn nngatnnntg gggccaaggc     360
accctggtga cggttagctc agc                                             383

<210> SEQ ID NO 51
<211> LENGTH: 380
<212> TYPE: DNA
<213> ORGANISM: Artificial
<220> FEATURE:
<223> OTHER INFORMATION: synthetic sequence
<220> FEATURE:
<221> NAME/KEY: misc_feature
<222> LOCATION: (292)..(339)
<223> OTHER INFORMATION: bases 292 - 339 encode a randomized sequence of
      any 16 amino acids
<220> FEATURE:
<221> NAME/KEY: misc_feature
<222> LOCATION: (343)..(345)
<223> OTHER INFORMATION: bases 343 - 345 encode any amino acid

<400> SEQUENCE: 51
caggtgcaat tgcaagaaag tggtccgggc ctggtgaaac cgagcgaaac cctgagcctg      60
acctgcaccg tttccggagg cagcattagc agctattatt ggagctggat tcgccagccg     120
cctgggaagg gtctcgagtg gattggctat atttattata gcggcagcac caactataat     180
ccgagcctga aaagccgggt gaccattagc gttgatactt cgaaaaacca gtttagcctg     240
aaactgagca gcgtgacggc ggcggatacg gccgtgtatt attgcgcgcg tnnnnnnnnn     300
nnnnnnnnnn nnnnnnnnnn nnnnnnnnnn nnnnnnnnng atnnntgggg ccaaggcacc     360
ctggtgacgg ttagctcagc                                                 380

<210> SEQ ID NO 52
<211> LENGTH: 383
<212> TYPE: DNA
<213> ORGANISM: Artificial
<220> FEATURE:
<223> OTHER INFORMATION: synthetic sequence
<220> FEATURE:
<221> NAME/KEY: misc_feature
<222> LOCATION: (295)..(342)
<223> OTHER INFORMATION: bases 295 - 342 encode a randomized sequence of
      any 16 amino acids
<220> FEATURE:
<221> NAME/KEY: misc_feature
<222> LOCATION: (346)..(348)
<223> OTHER INFORMATION: bases 346 - 348 encode any amino acid
```

<400> SEQUENCE: 52

```
caggtgcaat tggttcagag cggcgcggaa gtgaaaaaac cgggcgaaag cctgaaaatt      60
agctgcaaag gttccggata ttcctttacg agctattgga ttggctgggt gcgccagatg     120
cctgggaagg gtctcgagtg gatgggcatt atttatccgg cgatagcga tacccgttat     180
tctccgagct ttcagggcca ggtgaccatt agcgcggata aaagcattag caccgcgtat    240
cttcaatgga gcagctgaa agcgagcgat acggccatgt attattgcgc gcgtnnnnnn    300
nnnnnnnnnn nnnnnnnnnn nnnnnnnnnn nnnnnnnnnn nngatnnntg gggccaaggc    360
accctggtga cggttagctc agc                                             383
```

<210> SEQ ID NO 53
<211> LENGTH: 392
<212> TYPE: DNA
<213> ORGANISM: Artificial
<220> FEATURE:
<223> OTHER INFORMATION: synthetic sequence
<220> FEATURE:
<221> NAME/KEY: misc_feature
<222> LOCATION: (304)..(351)
<223> OTHER INFORMATION: bases 304 - 351 encode a randomized sequence of
      any 16 amino acids
<220> FEATURE:
<221> NAME/KEY: misc_feature
<222> LOCATION: (355)..(357)
<223> OTHER INFORMATION: bases 355 - 357 encode any amino acid

<400> SEQUENCE: 53

```
caggtgcaat tgcaacagtc tggtccgggc ctggtgaaac cgagccaaac cctgagcctg      60
acctgtgcga tttccggaga tagcgtgagc agcaacagcg cggcgtggaa ctggattcgc    120
cagtctcctg ggcgtggcct cgagtggctg ggccgtacct attatcgtag caatggtat    180
aacgattatg cggtgagcgt gaaaagccgg attaccatca acccggatac ttcgaaaaac    240
cagtttagcc tgcaactgaa cagcgtgacc ccggaagata cggccgtgta ttattgcgcg    300
cgtnnnnnnn nnnnnnnnnn nnnnnnnnnn nnnnnnnnnn nnnnnnnnnn ngatnnntgg    360
ggccaaggca ccctggtgac ggttagctca gc                                   392
```

<210> SEQ ID NO 54
<211> LENGTH: 30
<212> TYPE: DNA
<213> ORGANISM: Artificial
<220> FEATURE:
<223> OTHER INFORMATION: synthetic sequence

<400> SEQUENCE: 54

```
ggatttacct ttagctggaa ggcgatggcg                                       30
```

<210> SEQ ID NO 55
<211> LENGTH: 10
<212> TYPE: PRT
<213> ORGANISM: Artificial
<220> FEATURE:
<223> OTHER INFORMATION: synthetic sequence

<400> SEQUENCE: 55

Gly Phe Thr Phe Ser Trp Lys Ala Met Ala
1               5                   10

<210> SEQ ID NO 56
<211> LENGTH: 33
<212> TYPE: DNA
<213> ORGANISM: Artificial

```
<220> FEATURE:
<223> OTHER INFORMATION: synthetic sequence

<400> SEQUENCE: 56
agagcgagcc agggcattag cagctatctg gcg                                    33

<210> SEQ ID NO 57
<211> LENGTH: 11
<212> TYPE: PRT
<213> ORGANISM: Artificial
<220> FEATURE:
<223> OTHER INFORMATION: synthetic sequence

<400> SEQUENCE: 57

Arg Ala Ser Gln Gly Ile Ser Ser Tyr Leu Ala
1               5                   10

<210> SEQ ID NO 58
<211> LENGTH: 33
<212> TYPE: DNA
<213> ORGANISM: Artificial
<220> FEATURE:
<223> OTHER INFORMATION: synthetic sequence

<400> SEQUENCE: 58
agagcgagcc agggcattcg ggggtacctg ggg                                    33

<210> SEQ ID NO 59
<211> LENGTH: 11
<212> TYPE: PRT
<213> ORGANISM: Artificial
<220> FEATURE:
<223> OTHER INFORMATION: synthetic sequence

<400> SEQUENCE: 59

Arg Ala Ser Gln Gly Ile Arg Gly Tyr Leu Gly
1               5                   10

<210> SEQ ID NO 60
<211> LENGTH: 33
<212> TYPE: DNA
<213> ORGANISM: Artificial
<220> FEATURE:
<223> OTHER INFORMATION: synthetic sequence

<400> SEQUENCE: 60
agagcgagcc agggcatttt caagtacctg ggg                                    33

<210> SEQ ID NO 61
<211> LENGTH: 11
<212> TYPE: PRT
<213> ORGANISM: Artificial
<220> FEATURE:
<223> OTHER INFORMATION: synthetic sequence

<400> SEQUENCE: 61

Arg Ala Ser Gln Gly Ile Phe Lys Tyr Leu Ala
1               5                   10

<210> SEQ ID NO 62
<211> LENGTH: 33
<212> TYPE: DNA
<213> ORGANISM: Artificial
<220> FEATURE:
<223> OTHER INFORMATION: synthetic sequence

<400> SEQUENCE: 62
```

```
agagcgagcc agggcattat cgggtacctg ggc                                33
```

<210> SEQ ID NO 63
<211> LENGTH: 11
<212> TYPE: PRT
<213> ORGANISM: Artificial
<220> FEATURE:
<223> OTHER INFORMATION: synthetic sequence

<400> SEQUENCE: 63

```
Arg Ala Ser Gln Gly Ile Ile Gly Tyr Leu Gly
1               5                   10
```

<210> SEQ ID NO 64
<211> LENGTH: 33
<212> TYPE: DNA
<213> ORGANISM: Artificial
<220> FEATURE:
<223> OTHER INFORMATION: synthetic sequence

<400> SEQUENCE: 64

```
agagcgagcc agggcatttg gctgtacctg tcg                                33
```

<210> SEQ ID NO 65
<211> LENGTH: 11
<212> TYPE: PRT
<213> ORGANISM: Artificial
<220> FEATURE:
<223> OTHER INFORMATION: synthetic sequence

<400> SEQUENCE: 65

```
Arg Ala Ser Gln Gly Ile Trp Leu Tyr Leu Ser
1               5                   10
```

<210> SEQ ID NO 66
<211> LENGTH: 21
<212> TYPE: DNA
<213> ORGANISM: Artificial
<220> FEATURE:
<223> OTHER INFORMATION: synthetic sequence

<400> SEQUENCE: 66

```
gcagccagca gcttgcaaag c                                             21
```

<210> SEQ ID NO 67
<211> LENGTH: 7
<212> TYPE: PRT
<213> ORGANISM: Artificial
<220> FEATURE:
<223> OTHER INFORMATION: synthetic sequence

<400> SEQUENCE: 67

```
Ala Ala Ser Ser Leu Gln Ser
1               5
```

<210> SEQ ID NO 68
<211> LENGTH: 21
<212> TYPE: DNA
<213> ORGANISM: Artificial
<220> FEATURE:
<223> OTHER INFORMATION: synthetic sequence

<400> SEQUENCE: 68

```
tcggccagca gcttgcaaag c                                             21
```

<210> SEQ ID NO 69
<211> LENGTH: 7
<212> TYPE: PRT
<213> ORGANISM: Artificial
<220> FEATURE:
<223> OTHER INFORMATION: synthetic sequence

<400> SEQUENCE: 69

Ser Ala Ser Ser Leu Gln Ser
1               5

<210> SEQ ID NO 70
<211> LENGTH: 21
<212> TYPE: DNA
<213> ORGANISM: Artificial
<220> FEATURE:
<223> OTHER INFORMATION: synthetic sequence

<400> SEQUENCE: 70
gcggccagca gcttgcaaag c                                              21

<210> SEQ ID NO 71
<211> LENGTH: 7
<212> TYPE: PRT
<213> ORGANISM: Artificial
<220> FEATURE:
<223> OTHER INFORMATION: synthetic sequence

<400> SEQUENCE: 71

Ala Ala Ser Ser Leu Gln Ser
1               5

<210> SEQ ID NO 72
<211> LENGTH: 21
<212> TYPE: DNA
<213> ORGANISM: Artificial
<220> FEATURE:
<223> OTHER INFORMATION: synthetic sequence

<400> SEQUENCE: 72
cgcgccagca gcttgcaaag c                                              21

<210> SEQ ID NO 73
<211> LENGTH: 7
<212> TYPE: PRT
<213> ORGANISM: Artificial
<220> FEATURE:
<223> OTHER INFORMATION: synthetic sequence

<400> SEQUENCE: 73

Arg Ala Ser Ser Leu Gln Ser
1               5

<210> SEQ ID NO 74
<211> LENGTH: 21
<212> TYPE: DNA
<213> ORGANISM: Artificial
<220> FEATURE:
<223> OTHER INFORMATION: synthetic sequence

<400> SEQUENCE: 74
gccgccagca gcttgcaaag c                                              21

<210> SEQ ID NO 75
<211> LENGTH: 7
<212> TYPE: PRT
<213> ORGANISM: Artificial

<220> FEATURE:
<223> OTHER INFORMATION: synthetic sequence

<400> SEQUENCE: 75

Ala Ala Ser Ser Leu Gln Ser
1               5

<210> SEQ ID NO 76
<211> LENGTH: 316
<212> TYPE: DNA
<213> ORGANISM: Artificial
<220> FEATURE:
<223> OTHER INFORMATION: synthetic sequence

<400> SEQUENCE: 76

```
cagatgaccc agagcccgtc tagcctgagc gcgagcgtgg gtgatcgtgt gaccattacc      60
tgcagagcga gccagggcat tcgggggtac ctggggtggt accagcagaa accaggtaaa     120
gcaccgaaac tattaattta ttcggccagc agcttgcaaa gcgggtccc gtcccgtttt     180 agcggctctg gatccggcac tgattttacc ctgaccatta gcagcctgca acctgaagac     240
tttgcgacct attattgcca gcagtattct ggtatgcctt atacctttgg ccagggtacg     300
aaagttgaaa ttaaac                                                    316
```

<210> SEQ ID NO 77
<211> LENGTH: 212
<212> TYPE: PRT
<213> ORGANISM: Artificial
<220> FEATURE:
<223> OTHER INFORMATION: synthetic sequence

<400> SEQUENCE: 77

Gln Met Thr Gln Ser Pro Ser Ser Leu Ser Ala Ser Val Gly Asp Arg
1               5                   10                  15

Val Thr Ile Thr Cys Arg Ala Ser Gln Gly Ile Arg Gly Tyr Leu Gly
            20                  25                  30

Trp Tyr Gln Gln Lys Pro Gly Lys Ala Pro Lys Leu Leu Ile Tyr Ser
        35                  40                  45

Ala Ser Ser Leu Gln Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Tyr Ser Gly Met Pro Tyr Thr Phe
                85                  90                  95

Gly Gln Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

-continued

Arg Gly Glu Cys
    210

<210> SEQ ID NO 78
<211> LENGTH: 345
<212> TYPE: DNA
<213> ORGANISM: Artificial
<220> FEATURE:
<223> OTHER INFORMATION: synthetic sequence

<400> SEQUENCE: 78
ttggtggaaa gcggcggcgg cctggtgcaa ccgggcggca gcctgcgtct gagctgcgcg      60
gcctccggat ttacctttag cagctatgcg atgagctggg tgcgccaagc ccctgggaag     120
ggtctcgagt gggtgagcgc gattagcggt agcggcggca gcacctatta tgcggatagc     180
gtgaaaggcc gttttaccat ttcacgtgat aattcgaaaa cacccctgta tctgcaaatg     240
aacagcctgc gtgcggaaga tacggccgtg tattattgcg cgcgtcgtga ttttttttgct    300 cactttgatg tttggggcca aggcaccctg gtgacggtta gctca                     345

<210> SEQ ID NO 79
<211> LENGTH: 445
<212> TYPE: PRT
<213> ORGANISM: Artificial
<220> FEATURE:
<223> OTHER INFORMATION: synthetic sequence

<400> SEQUENCE: 79

Leu Val Glu Ser Gly Gly Gly Leu Val Gln Pro Gly Gly Ser Leu Arg
1               5                   10                  15

Leu Ser Cys Ala Ala Ser Gly Phe Thr Phe Ser Ser Tyr Ala Met Ser
            20                  25                  30

Trp Val Arg Gln Ala Pro Gly Lys Gly Leu Glu Trp Val Ser Ala Ile
        35                  40                  45

Ser Gly Ser Gly Gly Ser Thr Tyr Tyr Ala Asp Ser Val Lys Gly Arg
    50                  55                  60

Phe Thr Ile Ser Arg Asp Asn Ser Lys Asn Thr Leu Tyr Leu Gln Met
65                  70                  75                  80

Asn Ser Leu Arg Ala Glu Asp Thr Ala Val Tyr Tyr Cys Ala Arg Arg
                85                  90                  95

Asp Phe Phe Ala His Phe Asp Val Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

```
Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 80
<211> LENGTH: 993
<212> TYPE: DNA
<213> ORGANISM: Homo sapiens

<400> SEQUENCE: 80
gcctccacca agggtccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gggtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
```

-continued

```
cagaagagcc tctccctgtc tccgggtaaa tga                                    993
```

<210> SEQ ID NO 81
<211> LENGTH: 330
<212> TYPE: PRT
<213> ORGANISM: Homo sapiens

<400> SEQUENCE: 81

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
           100                 105                 110

Pro Ala Pro Glu Leu Leu Gly Gly Pro Ser Val Phe Leu Phe Pro Pro
       115                 120                 125

Lys Pro Lys Asp Thr Leu Met Ile Ser Arg Thr Pro Glu Val Thr Cys
   130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
           180                 185                 190

His Gln Asp Trp Leu Asn Gly Lys Glu Tyr Lys Cys Lys Val Ser Asn
       195                 200                 205

Lys Ala Leu Pro Ala Pro Ile Glu Lys Thr Ile Ser Lys Ala Lys Gly
   210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
           260                 265                 270

Asn Tyr Lys Thr Thr Pro Pro Val Leu Asp Ser Asp Gly Ser Phe Phe
       275                 280                 285

Leu Tyr Ser Lys Leu Thr Val Asp Lys Ser Arg Trp Gln Gln Gly Asn
   290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 82
<211> LENGTH: 318
<212> TYPE: DNA
<213> ORGANISM: Homo sapiens

<400> SEQUENCE: 82

```
gtggctgcac catctgtctt catcttcccg ccatctgatg agcagttgaa atctggaact    60
gcctctgttg tgtgcctgct gaataacttc tatcccagag aggccaaagt acagtggaag   120
gtggataacg ccctccaatc gggtaactcc caggagagtg tcacagagca ggacagcaag   180
gacagcacct acagcctcag cagcaccctg acgctgagca agcagactac gagaaacac   240
aaagtctacg cctgcgaagt cacccatcag ggcctgagct cgcccgtcac aaagagcttc   300
aacaggggag agtgttag                                                 318
```

<210> SEQ ID NO 83
<211> LENGTH: 105
<212> TYPE: PRT
<213> ORGANISM: Homo sapiens

<400> SEQUENCE: 83

```
Val Ala Ala Pro Ser Val Phe Ile Phe Pro Pro Ser Asp Glu Gln Leu
  1               5                  10                  15
Lys Ser Gly Thr Ala Ser Val Val Cys Leu Leu Asn Asn Phe Tyr Pro
             20                  25                  30
Arg Glu Ala Lys Val Gln Trp Lys Val Asp Asn Ala Leu Gln Ser Gly
         35                  40                  45
Asn Ser Gln Glu Ser Val Thr Glu Gln Asp Ser Lys Asp Ser Thr Tyr
     50                  55                  60
Ser Leu Ser Ser Thr Leu Thr Leu Ser Lys Ala Asp Tyr Glu Lys His
 65                  70                  75                  80
Lys Val Tyr Ala Cys Glu Val Thr His Gln Gly Leu Ser Ser Pro Val
                 85                  90                  95
Thr Lys Ser Phe Asn Arg Gly Glu Cys
            100                 105
```

<210> SEQ ID NO 84
<211> LENGTH: 330
<212> TYPE: DNA
<213> ORGANISM: Homo sapiens

<400> SEQUENCE: 84

```
accgtcctag gtcagcccaa ggctgccccc tcggtcactc tgttcccgcc ctcctctgag    60
gagcttcaag ccaacaaggc cacactggtg tgtctcataa gtgacttcta cccgggagcc   120
gtgacagtgg cctggaaggg agatagcagc cccgtcaagg cggagtggga gaccaccaca   180
ccctccaaac aaagcaacaa caagtacgcg gccagcagct atctgagcct gacgcctgag   240
cagtggaagt cccacagaag ctacagctgc caggtcacgc atgaagggag caccgtggag   300
aagacagtgg cccctacaga atgttcatag                                    330
```

<210> SEQ ID NO 85
<211> LENGTH: 109
<212> TYPE: PRT
<213> ORGANISM: Homo sapiens

<400> SEQUENCE: 85

```
Thr Val Leu Gly Gln Pro Lys Ala Ala Pro Ser Val Thr Leu Phe Pro
  1               5                  10                  15
Pro Ser Ser Glu Glu Leu Gln Ala Asn Lys Ala Thr Leu Val Cys Leu
             20                  25                  30
Ile Ser Asp Phe Tyr Pro Gly Ala Val Thr Val Ala Trp Lys Gly Asp
```

-continued

```
              35                    40                    45
Ser Ser Pro Val Lys Ala Gly Val Glu Thr Thr Thr Pro Ser Lys Gln
    50                    55                    60

Ser Asn Lys Tyr Ala Ala Ser Ser Tyr Leu Ser Leu Thr Pro Glu
65                    70                    75                    80

Gln Trp Lys Ser His Arg Ser Tyr Ser Cys Gln Val Thr His Glu Gly
                85                    90                    95

Ser Thr Val Glu Lys Thr Val Ala Pro Thr Glu Cys Ser
                100                   105
```